United States Patent
Yokoyama et al.

(10) Patent No.: US 11,676,461 B2
(45) Date of Patent: Jun. 13, 2023

(54) INFORMATION PROCESSING DEVICE, INFORMATION PROCESSING METHOD, AND PROGRAM FOR CONTROLLING HAPTICS BASED ON CONTEXT INFORMATION

(71) Applicant: SONY CORPORATION, Tokyo (JP)

(72) Inventors: Ryo Yokoyama, Tokyo (JP); Ikuo Yamano, Tokyo (JP); Yusuke Nakagawa, Kanagawa (JP); Takeshi Ogita, Tokyo (JP)

(73) Assignee: SONY CORPORATION, Tokyo (JP)

( * ) Notice: Subject to any disclaimer, the term of this patent is extended or adjusted under 35 U.S.C. 154(b) by 718 days.

(21) Appl. No.: 16/319,690

(22) PCT Filed: Jun. 5, 2017

(86) PCT No.: PCT/JP2017/020751
§ 371 (c)(1),
(2) Date: Jan. 22, 2019

(87) PCT Pub. No.: WO2018/042799
PCT Pub. Date: Mar. 8, 2018

(65) Prior Publication Data
US 2021/0287497 A1    Sep. 16, 2021

(30) Foreign Application Priority Data

Aug. 29, 2016   (JP) ............................. JP2016-166397

(51) Int. Cl.
*G08B 21/00*   (2006.01)
*G08B 3/00*    (2006.01)
(Continued)

(52) U.S. Cl.
CPC ................ *G08B 3/00* (2013.01); *A61B 5/01* (2013.01); *A61B 5/024* (2013.01); *A61B 5/1118* (2013.01);
(Continued)

(58) Field of Classification Search
CPC ........ G08B 3/00; A63F 13/213; A63F 13/285; A63F 13/212; A63F 13/215; A61B 5/024;
(Continued)

(56) References Cited

U.S. PATENT DOCUMENTS

| 5,623,903 A | 4/1997 | Ueda |
| 2006/0187215 A1* | 8/2006 | Rosenberg ............ G06F 3/0362 345/173 |

(Continued)

FOREIGN PATENT DOCUMENTS

| CN | 104049746 A | 9/2014 |
| CN | 105472527 A | 4/2016 |

(Continued)

*Primary Examiner* — Mark S Rushing
(74) *Attorney, Agent, or Firm* — Paratus Law Group, PLLC

(57) ABSTRACT

There is provided an information processing device to reduce the difference in way of feeling a tactile sense in accordance with a state or situation, the information processing device including: an acquisition unit configured to acquire context information concerning a state or a situation user of an external environment or context information concerning a user; and a modulation unit configured to modulate a control signal for controlling a haptics unit for presenting haptics to a predetermined part of the user on the basis of the context information having been acquired.

21 Claims, 20 Drawing Sheets

(51) Int. Cl.
*A63F 13/212* (2014.01)
*A63F 13/213* (2014.01)
*A63F 13/215* (2014.01)
*A63F 13/285* (2014.01)
*A61B 5/01* (2006.01)
*A61B 5/024* (2006.01)
*A61B 5/11* (2006.01)
*A61B 5/16* (2006.01)
*A61B 5/00* (2006.01)
*G06F 3/01* (2006.01)

(52) U.S. Cl.
CPC ............ *A61B 5/165* (2013.01); *A61B 5/4266* (2013.01); *A63F 13/212* (2014.09); *A63F 13/213* (2014.09); *A63F 13/215* (2014.09); *A63F 13/285* (2014.09); *G06F 3/016* (2013.01); *A61B 2560/0242* (2013.01)

(58) Field of Classification Search
CPC ..... A61B 5/165; A61B 5/4266; A61B 5/1118; A61B 5/01; A61B 2560/0242; G06F 3/016
USPC ........................................................ 340/407.1
See application file for complete search history.

(56) References Cited

U.S. PATENT DOCUMENTS

| | | | | |
|---|---|---|---|---|
| 2011/0090167 A1* | 4/2011 | Harris | ................... | G06F 3/043 345/173 |
| 2011/0285637 A1 | 11/2011 | Karkkainen | | |
| 2013/0225261 A1* | 8/2013 | Cruz-Hernandez | ..... | G06F 3/016 463/23 |
| 2014/0318699 A1* | 10/2014 | Longinotti-Buitoni | ...................... | D06M 11/83 156/247 |
| 2014/0347176 A1* | 11/2014 | Modarres | ................. | G08B 6/00 340/407.1 |
| 2015/0251089 A1* | 9/2015 | Komori | ................... | A63F 13/25 463/35 |
| 2015/0323995 A1* | 11/2015 | Lim | ........................ | G06F 3/016 345/174 |
| 2016/0001781 A1* | 1/2016 | Fung | ..................... | B60K 28/02 701/36 |
| 2016/0189493 A1* | 6/2016 | Rihn | ........................ | G08B 6/00 340/407.1 |
| 2016/0234572 A1* | 8/2016 | Dixit | .................. | G08B 21/0423 |
| 2016/0310844 A1* | 10/2016 | Yamashita | ............... | A63F 13/28 |

FOREIGN PATENT DOCUMENTS

| | | |
|---|---|---|
| JP | H06-197922 A | 7/1994 |
| JP | H07-103044 A | 4/1995 |
| JP | 2001-252265 A | 9/2001 |
| JP | 2004-092663 A | 3/2004 |
| JP | 2008-006037 A | 1/2008 |
| JP | 2008-125802 A | 6/2008 |
| JP | 2015-509801 A | 4/2015 |
| JP | 2015-170173 A | 9/2015 |
| JP | 2016-146173 A | 8/2016 |

* cited by examiner

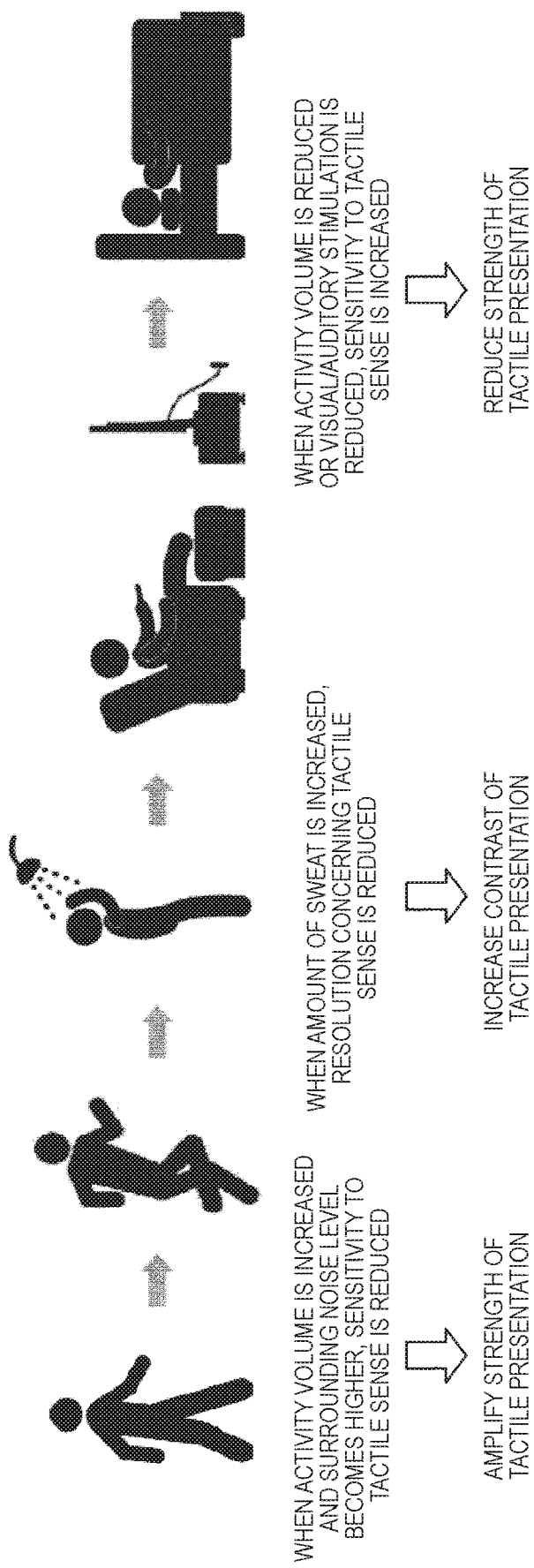

FIG. 2

 TACTILE SENSITIVITY VARIES DEPENDING ON AGE, OR TACTILE RESOLUTION VARIES DEPENDING ON DIFFERENCE IN HEIGHT

⇨ TACTILE PRESENTATION TUNED FOR INDIVIDUAL IS NECESSARY

 WAY OF FEELING TACTILE PRESENTATION VARIES BETWEEN INDIVIDUALS

⇨ IN SUCH CASE WHERE TACTILE PRESENTATION DEVICE IS SHARED AND USED BY PLURALITY OF USERS, IT IS NECESSARY TO MODULATE TACTILE DATA ON BASIS OF INDIVIDUAL INFORMATION

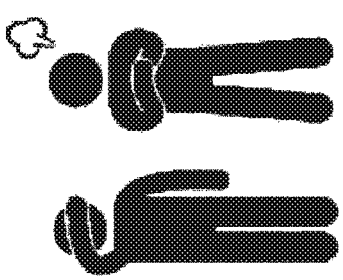

 TACTILE SENSITIVITY OR RESOLUTION IS CHANGED ALSO DEPENDING ON EMOTIONAL STATE ⇨ BY FEEDING BACK SENSED EMOTIONAL INFORMATION TO TACTILE PRESENTATION, TACTILE PRESENTATION EFFECT AS EXPECTED IS OBTAINED

INFORMATION PROCESSING DEVICE, INFORMATION PROCESSING METHOD, AND PROGRAM FOR CONTROLLING HAPTICS BASED ON CONTEXT INFORMATION

CROSS REFERENCE TO PRIOR APPLICATION

This application is a National Stage Patent Application of PCT International Patent Application No. PCT/JP2017/020751 (filed on Jun. 5, 2017) under 35 U.S.C. § 371, which claims priority to Japanese Patent Application No. 2016-166397 (filed on Aug. 29, 2016), which are all hereby incorporated by reference in their entirety.

TECHNICAL FIELD

The present disclosure relates to an information processing device, an information processing method, and a program.

BACKGROUND ART

Technologies for feeding back a tactile sense or a force sense (hereinafter, these senses on the body surface such as the skin will also be generally referred to as "haptics") to a user by means of vibrations, heat, electrical stimulation, or the like are being studied. As devices for feeding back haptics, a vibration actuator, a heat generating/absorbing element, an electrical stimulation device, and the like, for example, have been proposed. For example, Patent Literature 1 discloses an example of a technology of presenting haptics to a user.

CITATION LIST

Patent Literature

Patent Literature 1: JP 2015-170173A

DISCLOSURE OF INVENTION

Technical Problem

Particularly in recent years, not only mere presentation of haptics, but also reproduction of more realistic haptics is demanded. On the other hand, the way of feeling haptics may vary between individuals. Therefore, even in the case where a device for presenting haptics is operated in a predetermined mode, for example, the way of feeling haptics may vary between users. In addition, the way of feeling haptics may vary even in the same user in accordance with a state or situation. That is, even in the case where a device for presenting haptics is operated in a predetermined mode, the way of feeling haptics may vary in accordance with the state or situation.

Therefore, the present disclosure proposes an information processing device, an information processing method, and a program that can reduce the difference in way of feeling haptics in accordance with the state or situation.

Solution to Problem

According to the present disclosure, there is provided an information processing device including: an acquisition unit configured to acquire context information concerning a state or a situation of an external environment or context information concerning a user; and a modulation unit configured to modulate a control signal for controlling a haptics unit for presenting haptics to a predetermined part of the user on the basis of the context information having been acquired.

In addition, according to the present disclosure, there is provided an information processing method, including: acquiring, by using a computer system, context information concerning a state or a situation of an external environment or context information concerning a user; and modulating, by using the computer system, a control signal for controlling a haptics unit for presenting haptics to a predetermined part of the user on the basis of the context information having been acquired.

In addition, according to the present disclosure, there is provided a program causing a computer system to execute: acquiring context information concerning a state or a situation of an external environment or context information concerning a user; and modulating a control signal for controlling a haptics unit for presenting haptics to a predetermined part of the user on the basis of the context information having been acquired.

Advantageous Effects of Invention

According to the present disclosure as described above, an information processing device, an information processing method, and a program that can reduce the difference in way of feeling haptics in accordance with the state or situation are provided.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is an explanatory diagram for describing an example of changes in the way of feeling a tactile sense.

FIG. 2 is an explanatory diagram for describing an example of changes in the way of feeling a tactile sense.

MODE(S) FOR CARRYING OUT THE INVENTION

Figure 3:
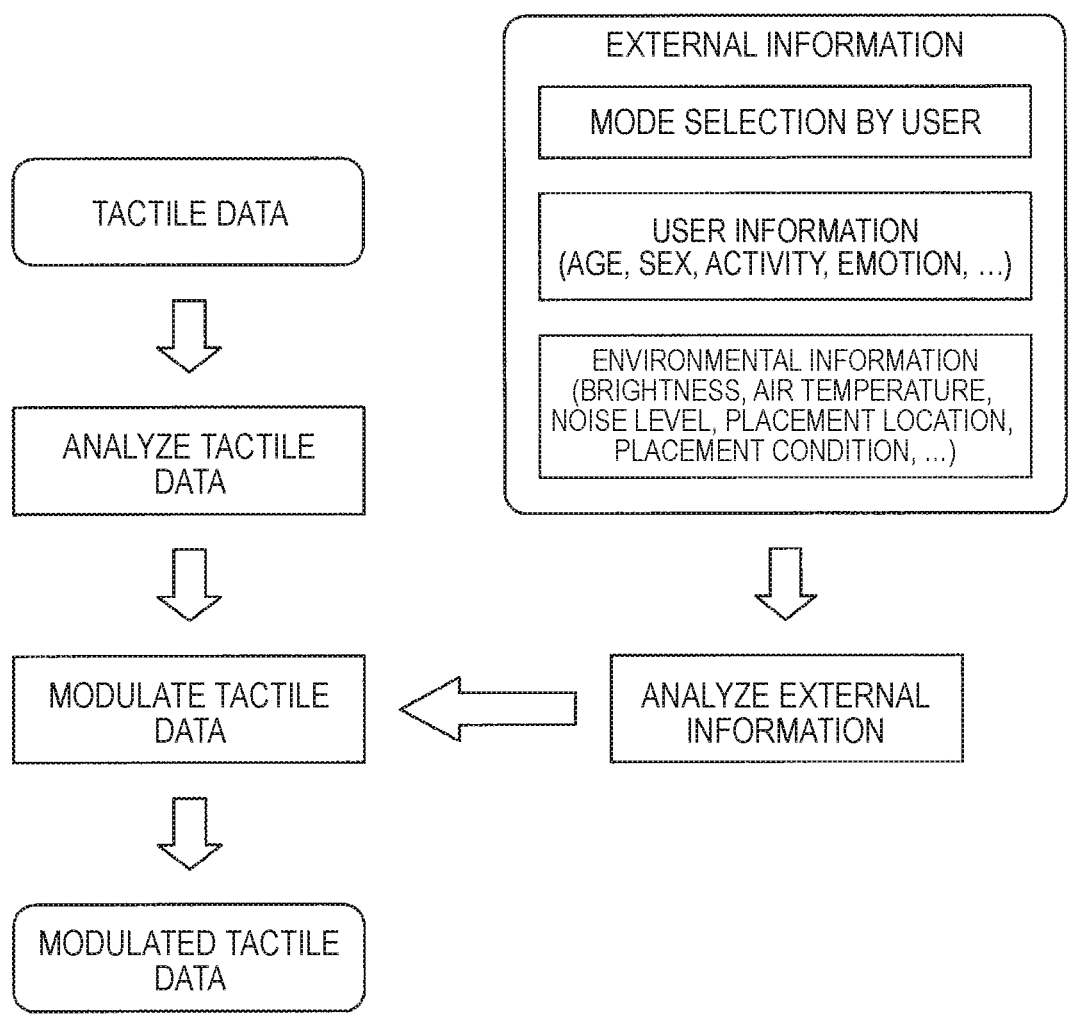
FIG. 3 is an explanatory diagram for describing an overview of an operation of an information processing system according to an embodiment of the present disclosure.

Hereinafter, (a) preferred embodiment (s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Studies concerning tactile feedback
2. Embodiment
2.1. Operation overview
2.2. System configuration
2.3. Functional configuration
2.4. Processing
3. Examples
3.1. Example 1: example of control in accordance with user
3.2. Example 2: example of control in accordance with external environment
3.3. Example 3: other control examples
4. Hardware configuration
5. Conclusion

1. STUDIES CONCERNING TACTILE FEEDBACK

As a method in which a so-called information processing device (or an information processing system including the information processing device), such as a personal computer (PC), a smartphone, a tablet terminal, and the like, feeds back information to a user, a method of giving feedback by means of video, voice, and sound, or the like is generally known, for example. As an example of such a technology for feeding back information to the user, a technology for feeding back a tactile sense by means of vibrations, heat, electrical stimulation, or the like, is being studied. As specific examples, a vibration actuator, a heat generating/absorbing element, an electrical stimulation device, and the like, for example, have been proposed as a device for feeding back a tactile sense. Particularly in recent years, not only mere presentation of a tactile sense, but also reproduction of a more realistic tactile sense is demanded.

On the other hand, the way of feeling a tactile sense may vary in accordance with a change in various states or situations. For example. FIG. 1 is an explanatory diagram for describing an example of changes in the way of feeling a tactile sense, and shows an example of changes in the way of feeling a tactile sense associated with changes in various states or situations, such as changes in the state of the user, an external environment, or the like.

For example, the way of feeling a tactile sense may be changed in accordance with a change in activity volume. As a specific example, when the activity volume is increased by the user starting running from the state of standing still or walking, the tactile sensitivity of the user tends to be reduced. In contrast to this, when the activity volume is reduced in association with a rest or sleep, the tactile sensitivity of the user tends to be increased.

In addition, the tactile sensitivity of the user may be changed in accordance with a change in a surrounding environment. As a specific example, when the noise level around the user is increased, the tactile sensitivity of the user tends to be reduced. In contrast to this, when visual stimulation or auditory stimulation is reduced, the tactile sensitivity of the user tends to be increased.

In addition, the way of feeling a tactile sense (hereinafter also referred to as "tactile resolution") may be changed in accordance with the amount of sweat. As a specific example, when the amount of sweat is increased, the tactile resolution is reduced, and the user may be less likely to feel a more delicate tactile change.

In addition, the way of feeling a tactile sense may vary between individuals. For example, FIG. 2 is an explanatory diagram for describing an example of changes in the way of feeling a tactile sense, and shows an example of a difference in way of feeling a tactile sense between users.

Specifically, the tactile sensitivity may be changed in accordance with the age. In addition, the tactile resolution may vary in accordance with the difference in physical characteristics such as the height. In addition, as another example, the tactile sensitivity or tactile resolution may be changed in accordance with the emotional state. Of course, the way of feeling a tactile sense may vary individually between different users.

As described above, the way of feeling a tactile sense may vary in accordance with a change in various states or situations, and an individual difference may also occur between users. Therefore, even if, assuming reproduction of a certain situation, presentation of a tactile sense in accordance with the situation is performed in a constant mode, the way of feeling of the user may vary from moment to moment, and if the user to be targeted for presentation of a tactile sense varies, the way of feeling may vary between users.

In view of the situations as described above, the present disclosure proposes an example of a mechanism for reducing the difference in way of feeling a tactile sense associated with a change in various states or situations and the difference in way of feeling a tactile sense between respective users.

Specifically, paying attention to the example shown in FIG. 1, under such a situation where the tactile sensitivity is reduced, a tactile sense that the user feels in the same manner as before the sensitivity is reduced is reproduced by amplifying the strength of tactile presentation, for example. In addition, under such a situation where the tactile sensitivity is increased, the strength of tactile presentation may be reduced, for example. In addition, under such a situation where the tactile resolution is reduced, a tactile sense that the user feels in the same manner as before the tactile resolution is reduced is reproduced by increasing the contrast of tactile presentation so that the user is more likely to feel a tactile change.

In addition, paying attention to the example shown in FIG. 2, the strength or contrast of tactile presentation may be tuned in accordance with the age or physical characteristics of the user. In addition, by sensing the emotion of the user and feeding back a result of the sensing to tactile presentation, it is expected that an assumed tactile sense can be presented to the user regardless of an emotional change. In addition, the strength or contrast of tactile presentation may be tuned for each user. With such a configuration, even under such a situation where a device for presenting a tactile sense to a user is shared among a plurality of users, a tactile sense felt in the same manner among the plurality of users is reproduced for each user.

Therefore, as an embodiment of the present disclosure, details of a mechanism for achieving the above-described control will be described below.

2. EMBODIMENT

First, a basic configuration of an information processing system according to an embodiment of the present disclosure will be described.

2.1. Operation Overview

First, an overview of an operation of an information processing system according to an embodiment of the present disclosure will be described with reference to FIG. 3 to FIG. 6. For example, FIG. 3 is an explanatory diagram for describing an overview of an operation of the information processing system according to the present embodiment.

As shown in FIG. 3, for feeding back a tactile sense to the user, the information processing system according to the present embodiment analyzes tactile data for driving a haptics unit such as a vibration actuator or an electrical stimulation device, and on the basis of the analysis result, modulates the tactile data. At this time, the information processing system analyzes external information (that is, context information in accordance with various states or situations), such as a mode selected by the user, user information, and environmental information, and modulates the tactile data in accordance with the analysis result. Then, by driving the haptics unit on the basis of the modulated tactile data, the information processing system feeds back a tactile sense to the user. With such a configuration, the information processing system according to the present embodiment controls a tactile sense to be fed back to the user by appropriately changing the contents of processing related to modulation of tactile data in accordance with the external information.

Figure 4:
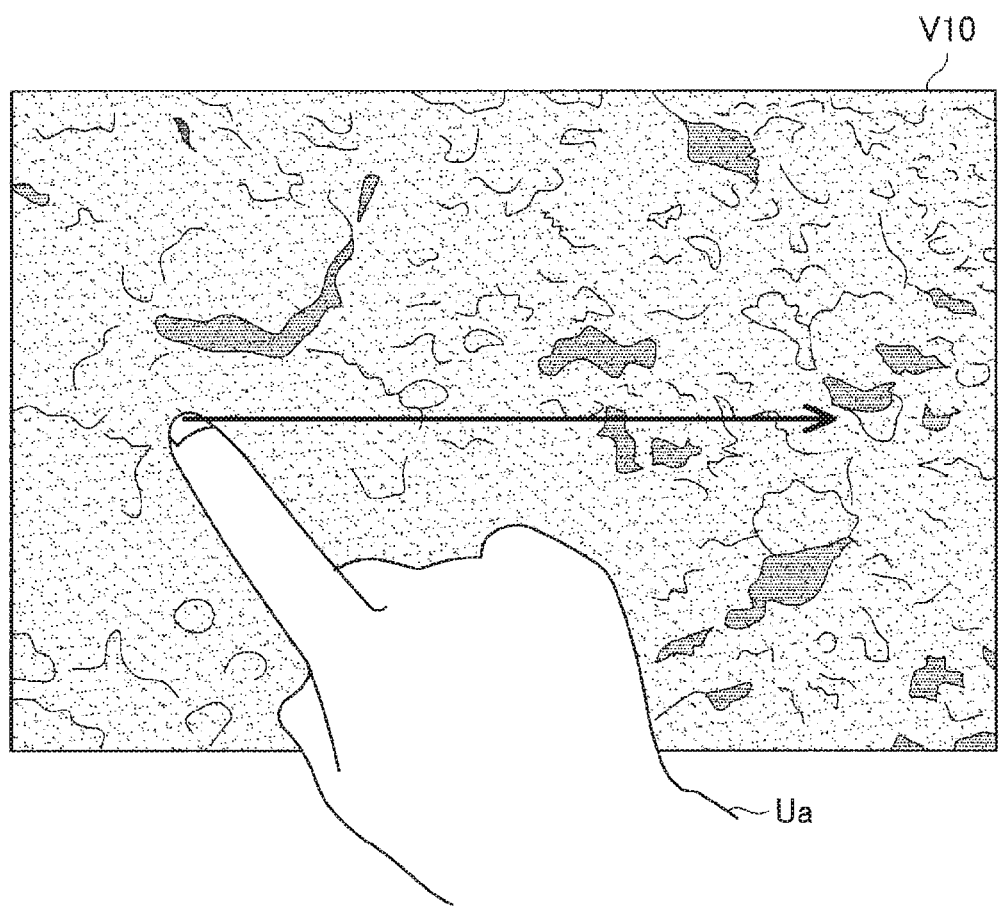
FIG. 4 is an explanatory diagram for describing an overview of an operation related to modulation of tactile data.
Figure 5:
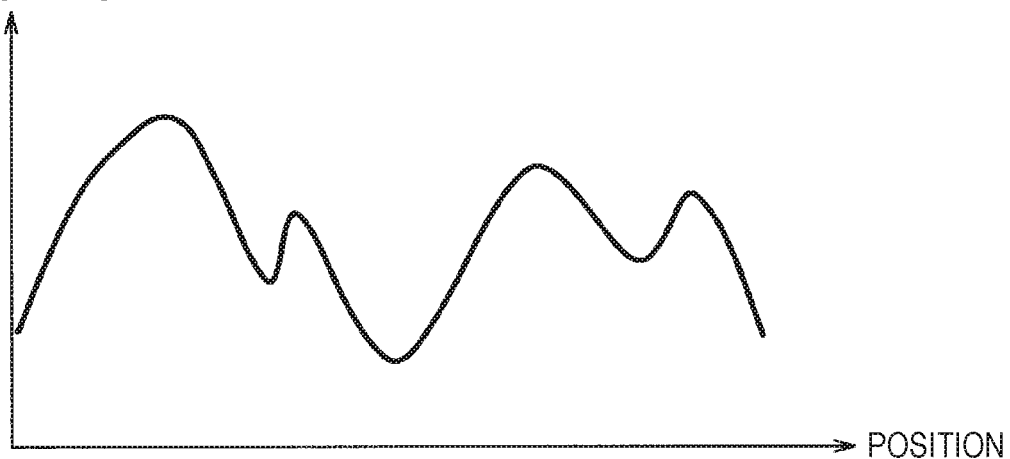
FIG. 5 is an explanatory diagram for describing an overview of an operation related to modulation of tactile data.
Figure 6:
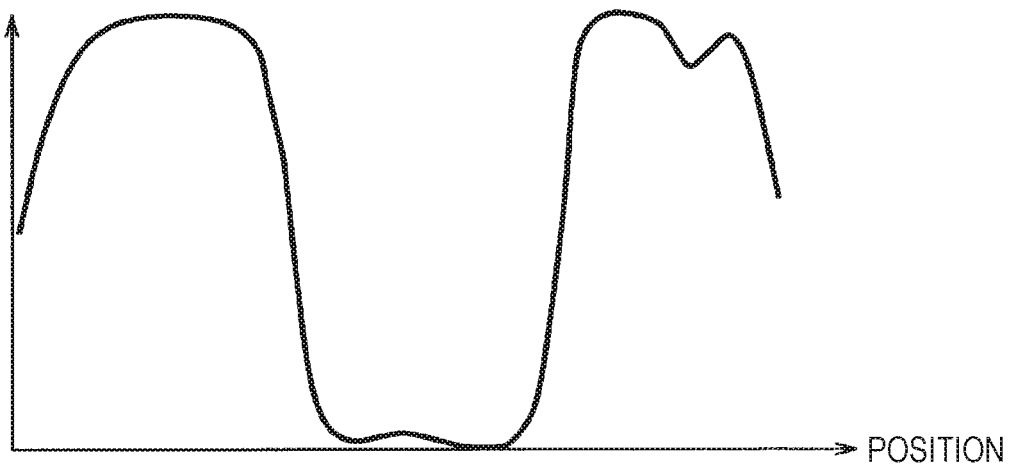
FIG. 6 is an explanatory diagram for describing an overview of an operation related to modulation of tactile data.

Here, an overview of an operation related to modulation of tactile data will be described with reference to FIG. 4 to FIG. 6. FIG. 4 to FIG. 6 are explanatory diagrams for describing an overview of an operation related to modulation of tactile data. For example, FIG. 4 shows a situation where the user is tracing a screen in which an image V10 such as irregularities is presented with a manipulation member Ua such as a finger. At this time, by driving the haptics unit in accordance with the position on the screen traced with the manipulation member Ua, the information processing system feeds back a tactile sense in accordance with the image presented at that position to the user.

For example, FIG. 5 shows an example of tactile data. In FIG. 5, the horizontal axis indicates the position (that is, the position in the image V10) on the screen. In addition, the vertical axis schematically indicates the strength of a tactile sense to be presented to the user, which, in the case of feeding back a tactile sense to the user by means of vibrations, for example, may be equivalent to the strength of the vibrations. In contrast to this, FIG. 6 shows an example of tactile data after modulation. That is, in FIG. 6, the horizontal axis and the vertical axis are similar to those in the example shown in FIG. 5. More specifically. FIG. 6 shows an example of the case of modulating tactile data such that the contrast of the tactile data is improved. With such control, it is possible to control a tactile sense to be presented to the user such that the user is more likely to feel a more delicate tactile change, such as a tactile change by means of fine irregularities, or the like, for example.

Note that the tactile data shown in FIG. 5 and FIG. 6 is merely an example, and is not necessarily limited to the examples shown in FIG. 5 and FIG. 6. For example, a plurality of types of receptors for a human to feel a tactile sense exist, and the frequency of vibrations by which a neural activity of each receptor is reduced varies between receptors. In view of such a situation, tactile data may include data about the tactile strengths as shown in FIG. 5 and FIG. 6 regarding a plurality of frequency components, for example. Note that details of the above-described example will be described later separately.

An overview of the operation of the information processing system according to an embodiment of the present disclosure has been described above with reference to FIG. 3 to FIG. 6. Note that the mechanism for controlling a tactile sense to be presented to the user by the information processing system according to the present embodiment modulating tactile data in accordance with external information will be described hereinafter in more detail.

2.2. System Configuration

Figure 7:
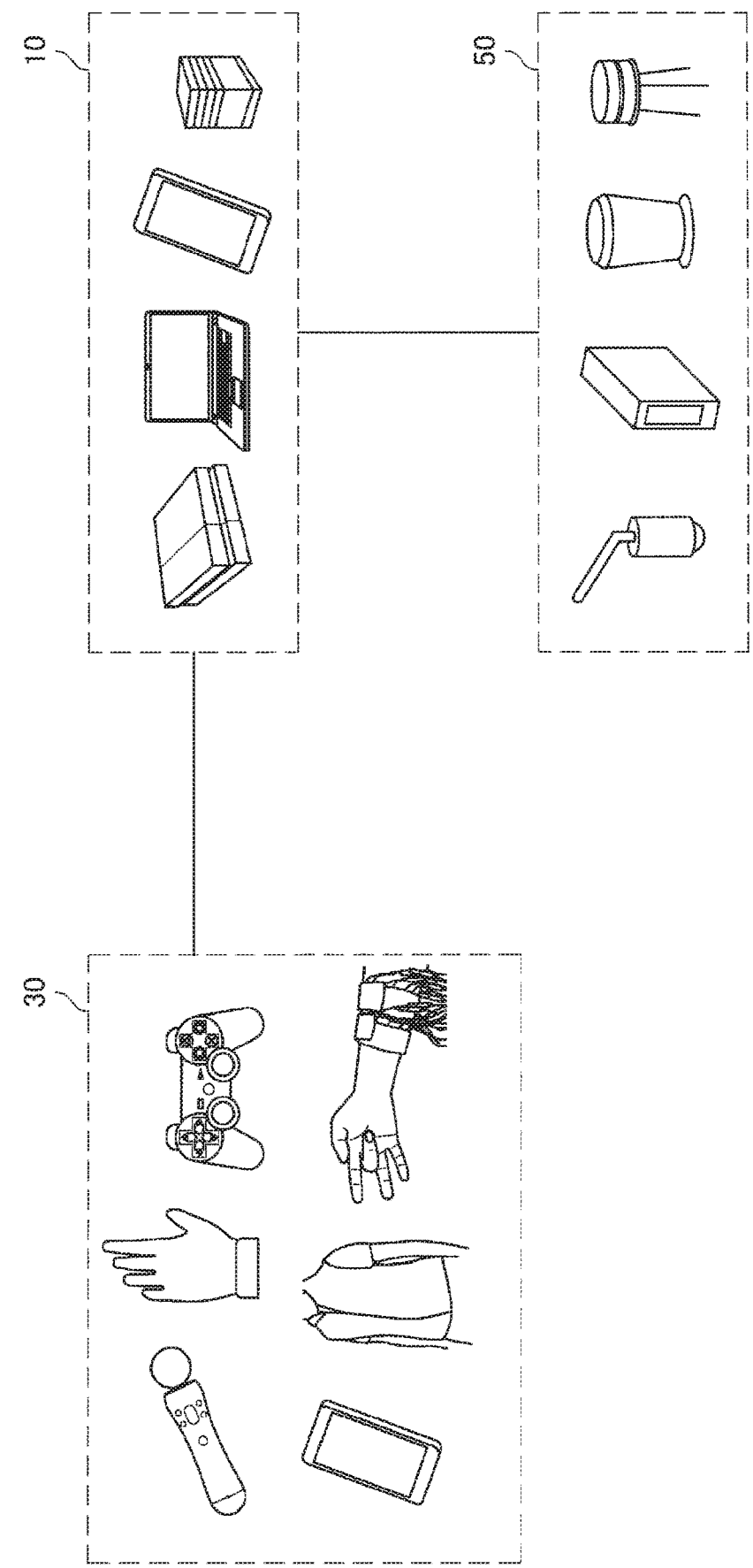
FIG. 7 is an explanatory diagram for describing an example of a system configuration of the information processing system according to the embodiment.

Next, an example of a schematic system configuration of the information processing system according to an embodiment of the present disclosure will be described with reference to FIG. 7. FIG. 7 is an explanatory diagram for describing an example of a system configuration of the information processing system according to the present embodiment.

As shown in FIG. 7, an information processing system 1 according to the present embodiment includes an information processing device 10, a haptics unit 30, and an external information acquisition device 50. Each of the information processing device 10, the haptics unit 30, and the external information acquisition device 50 is configured to be capable of transmitting/receiving information to each other via a predetermined network. Note that the type of the network connecting the information processing device 10, the haptics unit 30, and the external information acquisition device 50 is not particularly limited. As a specific example, the network may include a so-called wireless network such as a network based on the Wi-Fi (registered trademark) standard. In addition, as another example, the network may include the Internet, a leased line, a local area network (LAN), a wide area network (WAN), or the like. In addition, the network may include a plurality of networks, or may be configured as a wired network at least partially.

The haptics unit 30 feeds back a tactile sense to a user who holds the haptics unit 30 on the basis of control from the information processing device 10 which will be described later. As a specific example, the haptics unit 30 includes a vibration device such as a vibration actuator, and may simulate a tactile sense by vibrating the vibration device. In addition, as another example, the haptics unit 30 includes an electrical stimulation device, and may feed back a tactile sense by applying electric simulation to the skin with the electrical stimulation device to induce firing of neurons.

In addition, the haptics unit 30 may be configured as a so-called wearable device to be placed at a predetermined part of the user, for example. In this case, for example, the haptics unit 30 may feed back a tactile sense to the placed part. In addition, as another example, the haptics unit 30 may be configured as a controller of a game console or the like. In this case, the haptics unit 30 may feed back a tactile sense to the hand of the user grasping the housing of the haptics unit 30. In addition, an information processing device such as a so-called smartphone may be utilized as the haptics unit 30. As a specific example, by vibrating an actuator of the smartphone, a tactile sense may be fed back to the user grasping the smartphone.

The external information acquisition device 50 is a component for acquiring context information in accordance with various states or situations, such as information about an external environment, information concerning the user, and the like, as external information. Note that, in the present disclosure, "acquisition" of external information may include performing sensing with a sensor or the like and externally receiving data including sensing data, or reading the data from a recording medium.

As a specific example, the external information acquisition device 50 includes various sensors for acquiring information about the brightness, noise, temperature, humidity, and the like of an external environment, and may acquire information about the external environment as external information with the sensors. In addition, the external information acquisition device 50 includes an imaging unit that images the external environment, and may acquire an image captured by the imaging unit as external information.

In addition, as another example, the external information acquisition device 50 includes various sensors for acquiring information about the activity volume, heart rate, body temperature, amount of sweat, and the like of the user, and may acquire information indicating the state of the user with the sensors as external information. In addition, the external information acquisition device 50 includes an imaging unit that images the user, and may acquire an image captured by the imaging unit as external information indicating the state of the user. In addition, on the basis of the result of acquiring the information indicating the state of the user, it is also possible to estimate the emotion of the user (for example, joy, anger, sorrow, pleasure, or the like) or the way of feeling of the user (for example, pleasant, unpleasant, or the like). For example, the emotion of the user may be estimated by carrying out an image analysis on an image obtained by imaging the face of the user. Note that, in this case, the external information acquisition device 50 may estimate (or recognize) the emotion of the user or the way of feeling of the user, and may acquire the estimation result as external information. In addition, as another example, an output destination (for example, the information processing device 10) of the result of acquiring the state of the user may estimate the emotion of the user or the way of feeling of the user.

In addition, as another example, the external information acquisition device 50 may acquire information indicating an attribute of the user, such as the age, sex, or the like of the user, as external information. In this case, for example, the external information acquisition device 50, may access a predetermined server on the basis of identification information input by the user to acquire information indicating an attribute of the user correlated to the identification information.

In addition, as another example, the external information acquisition device 50 may acquire, as external information, information indicating an operation mode for controlling the operation of the information processing system 1 designated by the user via a predetermined input unit. For example, by receiving designation of an operation mode concerning tactile presentation by the haptics unit 30 via the predetermined input unit, the external information acquisition device 50 may acquire information indicating the operation mode. Note that examples of the operation mode concerning tactile presentation include a mode for controlling (for example, increasing) the strength of tactile presentation and a mode for controlling (for example, increasing) the contrast of tactile presentation.

In the foregoing manner, the external information acquisition device 50 acquires external information, and outputs the acquired external information to the information processing device 10. Accordingly, it is possible for the information processing device 10 to recognize a change in the external environment, a change in the state of the user, an attribute of the user, and the like on the basis of the external information.

By controlling the operation of the haptics unit 30, the information processing device 10 feeds back a tactile sense to the user holding the haptics unit 30. As a specific example, by reading tactile data (for example, data shown in FIG. 2) stored in a predetermined storage area and driving the haptics unit 30 on the basis of the tactile data, the information processing device 10 feeds back a tactile sense to the user.

In addition, upon acquiring external information such as information about the external environment or information concerning the user from the external information acquisition device 50 and modulating the external information on the basis of the tactile data, the information processing device 10 may drive the haptics unit 30 on the basis of the tactile data after modulation. With such a configuration, for example, it is possible for the information processing device 10 to control a tactile sense to be fed back so as to reduce the difference in way of feeling a tactile sense in accordance with a change in the external environment or the state of the user or the difference in way of feeling a tactile sense between different users. Note that details of the present control will be described later separately together with specific examples.

Note that the system configuration shown in FIG. 7 is merely an example, and the system configuration of the information processing system 1 according to the present embodiment is not necessarily limited only to the example shown in FIG. 7.

As a specific example, at least some, two or more components among the information processing device 10, the haptics unit 30, and the external information acquisition device 50 may be configured integrally.

An example of the schematic system configuration of the information processing system according to an embodiment of the present disclosure has been described above with reference to FIG. 7.

2.3. Functional Configuration

Figure 8:
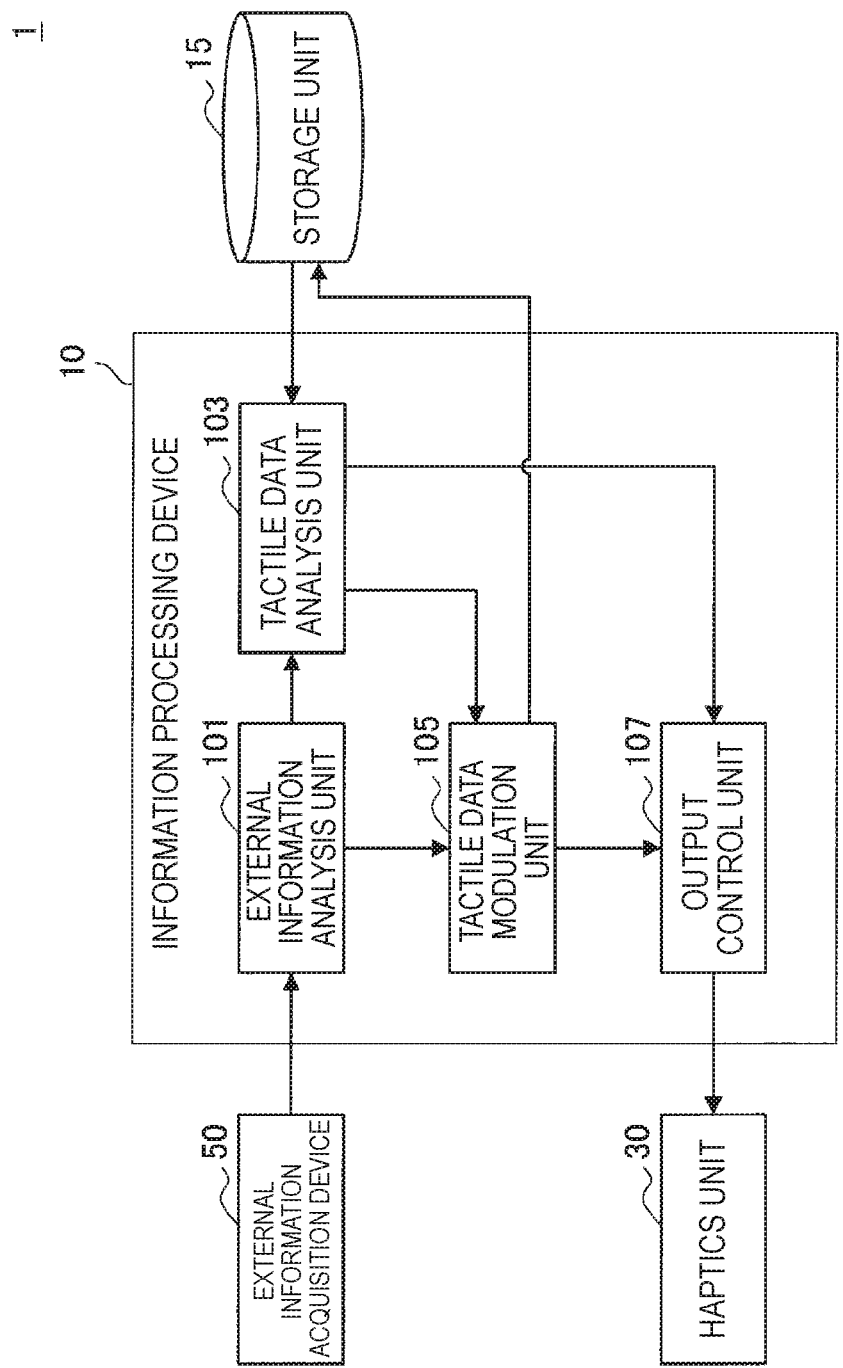
FIG. 8 is a block diagram showing an example of a functional configuration of the information processing system according to the embodiment.

Subsequently, as an example of a functional configuration of the information processing system according to an embodiment of the present disclosure, description will be given particularly paying attention to a configuration of the information processing device 10 with reference to FIG. 8. FIG. 8 is a block diagram showing an example of a functional configuration of the information processing system according to the present embodiment.

As shown in FIG. 8, the information processing system 1 according to the present embodiment includes the information processing device 10, the haptics unit 30, the external information acquisition device 50, and a storage unit 15. Since the haptics unit 30 and the external information acquisition device 50 are equivalent to the haptics unit 30 and the external information acquisition device 50 described with reference to FIG. 7, detailed description will be omitted.

The storage unit 15 is a storage area for temporarily or permanently storing various types of data. For example, the aforementioned tactile data may be stored in the storage unit 15. In addition, data for the information processing device 10 to execute various functions may be stored in the storage unit 15. As a more specific example, data (for example, libraries) for executing various applications, management data for managing various settings and the like, and the like may be stored in the storage unit 15.

The information processing device 10 includes an external information analysis unit 101, a tactile data analysis unit 103, a tactile data modulation unit 105, and an output control unit 107.

The external information analysis unit 101 acquires external information (context information) from the external information acquisition device 50, and analyzes the acquired external information to recognize a change in various states or situations such as the external environment or the state of the user, recognize a user individually (in other words, acquire information concerning the user), and the like. Note that, of the external information analysis unit 101, a portion that acquires external information from the external information acquisition device 50 is equivalent to an example of an "acquisition unit".

As a specific example, the external information analysis unit 101 acquires a detection result of the brightness, noise, temperature, humidity . . . or the like of the external environment from the external information acquisition device 50 to recognize the state of the external environment on the basis of the detection result. In addition, the external information analysis unit 101 may acquire an image obtained by imaging the external environment from the external information acquisition device 50 to recognize the state or situation of the external environment on the basis of the image.

In addition, as another example, the external information analysis unit 101 acquires a detection result of the activity volume, heart rate, body temperature, amount of sweat, or the like of the user from the external information acquisition device 50 to recognize the state of the user on the basis of the detection result. In addition, the external information analysis unit 101 may acquire an image obtained by imaging the user from the external information acquisition device 50 to recognize the state of the user, the situation in which the user is placed, or the like on the basis of the image. The external information analysis unit 101 may carry out analysis processing on the image obtained by imaging the user to estimate the emotion of the user or the way of feeling of the user on the basis of a result of the analysis processing.

In addition, as another example, the external information analysis unit 101 may acquire information indicating an attribute of the user, such as the age, sex, or the like of the user, from the external information acquisition device 50 to recognize or identify each user. With such a configuration, even under such a situation where the haptics unit 30 is shared among a plurality of users, for example, it is possible for the information processing device 10 to identify a user holding the haptics unit 30.

In addition, as another example, the external information analysis unit 101 may acquire information indicating an operation mode designated by the user from the external information acquisition device 50 via a predetermined input unit to recognize contents of an operation designated by the user. As a specific example, the external information analysis unit 101 may acquire information indicating the user-designated operation mode concerning tactile presentation by the haptics unit 30 to recognize contents of control designated by the user regarding an operation related to tactile presentation.

In the foregoing manner, the external information analysis unit 101 analyzes the external information acquired from the external information acquisition device 50, and outputs an analysis result to the tactile data modulation unit 105. In addition, the external information analysis unit 101 may output the analysis result of the external information to the tactile data analysis unit 103.

The tactile data analysis unit 103 reads tactile data corresponding to a tactile sense to be presented to the user from the storage unit 15. As a specific example, in accordance with contents of a manipulation on a predetermined input unit (illustration omitted) such as a touch panel, the tactile data analysis unit 103 may read tactile data for presenting a tactile sense in accordance with the manipulation from the storage unit 15. In addition, as another example, in accordance with a result of playing back various types of content such as video and sound, the tactile data analysis unit 103 may read tactile data corresponding to a tactile sense to be presented in association with playback of the content from the storage unit 15. Of course, the above-described example is merely an example, and as long as the tactile data analysis unit 103 is capable of specifying a tactile sense to be presented to the user and reading tactile data corresponding to the tactile sense from the storage unit 15, a condition therefor is not particularly limited.

Next, the tactile data analysis unit 103 carries out analysis processing on the read tactile data to recognize contents of the tactile data. As a specific example, on the basis of the analysis processing, the tactile data analysis unit 103 may recognize the tactile strength in accordance with the position or target at which a manipulation has been performed. In addition, in the case where the tactile data includes data about the tactile strength for each of a plurality of frequency components, the tactile data analysis unit 103 may recognize the tactile strength in accordance with the position or target at which the manipulation has been performed for each frequency component.

Then, the tactile data analysis unit 103 outputs the read tactile data and information indicating an analysis result of the tactile data to the tactile data modulation unit 105. Accordingly, it is possible for the tactile data modulation unit 105 to recognize the tactile data to be targeted for processing and contents of the tactile data.

In addition, as another example, in the case where tactile data after modulation has already been stored in the storage unit 15, the tactile data analysis unit 103 may acquire the analysis result of external information from the external information analysis unit 101, and may read the tactile data after modulation corresponding to the analysis result from the storage unit 15. Specifically, the tactile data analysis unit 103 may specify a tactile sense to be presented to the user on the basis of a predetermined condition, and extract tactile data (for example, tactile data correlated to the analysis result) modulated on the basis of the acquired analysis result of the external information, among pieces of tactile data corresponding to the tactile sense, from the storage unit 15. Note that the tactile data after modulation may be generated by the tactile data modulation unit 105 which will be described later, and may be stored in the storage unit 15. In addition, in the case where the tactile data after modulation is read, the tactile data analysis unit 103 may output the tactile data to the output control unit 107.

The tactile data modulation unit 105 modulates the tactile data in accordance with the analysis result of external information. For example, the tactile data modulation unit 105 acquires tactile data to be targeted for modulation and information indicating an analysis result of the tactile data from the tactile data analysis unit 103. In addition, the tactile data modulation unit 105 acquires information indicating the analysis result of the external information from the external information analysis unit 101. The tactile data modulation unit 105 determines modulation processing to be carried out on the tactile data on the basis of the analysis result of the external information, and carries out the determined modulation processing on the acquired tactile data.

For example, the tactile data modulation unit 105 may modulate the tactile data such that the tactile strength becomes higher in accordance with a recognition result of various states or situations based on the analysis result of the external information. In addition, as another example, the tactile data modulation unit 105 may modulate tactile data such that the contrast of tactile presentation becomes higher in accordance with a recognition result of various states or situations based on the analysis result of the external information.

Note that the tactile data modulation unit 105 may carry out different modulation processing for each frequency component included in tactile data. For example, FIG. 9 to FIG. 14 are explanatory diagrams for describing examples of processing related to modulation of tactile data, and show examples of the cases of carrying out modulation processing for respective frequency bands of low, middle, and high ranges. Note that, in the present description, the "low range" shall indicate a frequency band of 0 to 50 Hz, the "middle range" shall indicate a frequency band of 50 to 200 Hz, and the "high range" shall indicate a frequency band of 200 to 400 Hz. In addition, in FIG. 8 to FIG. 13, the horizontal axis indicates the frequency, and the vertical axis indicates gains for adjusting the tactile strength (for example, the strength of vibrations).

Figure 9:
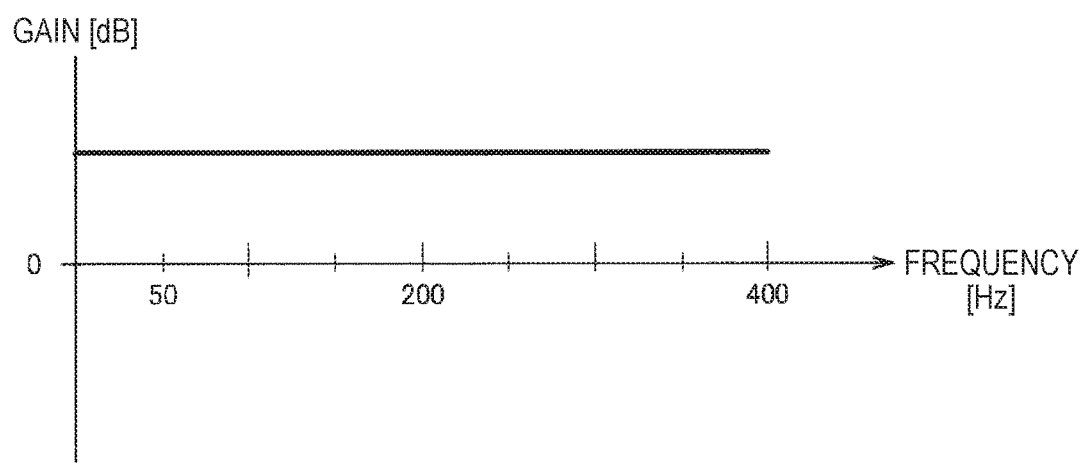
FIG. 9 is an explanatory diagram for describing an example of processing related to modulation of tactile data.
Figure 10:
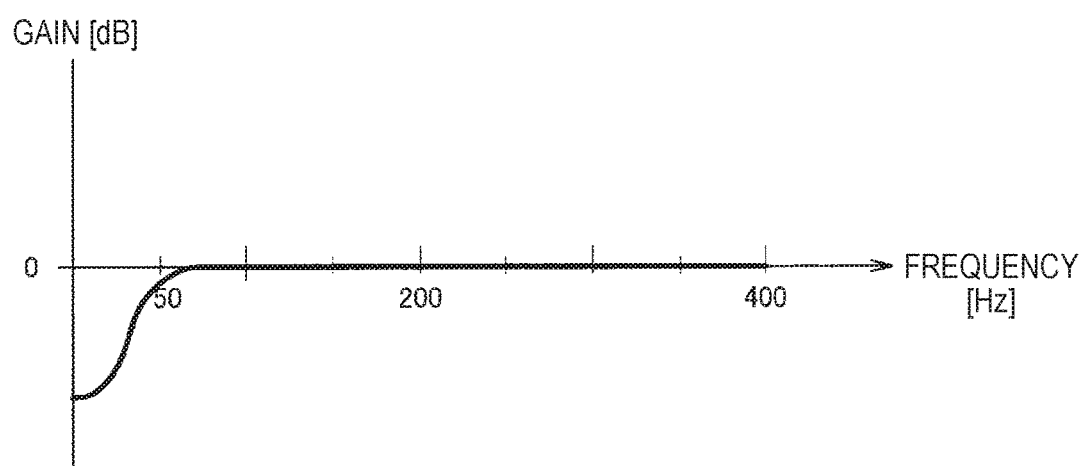
FIG. 10 is an explanatory diagram for describing an example of processing related to modulation of tactile data.
Figure 11:
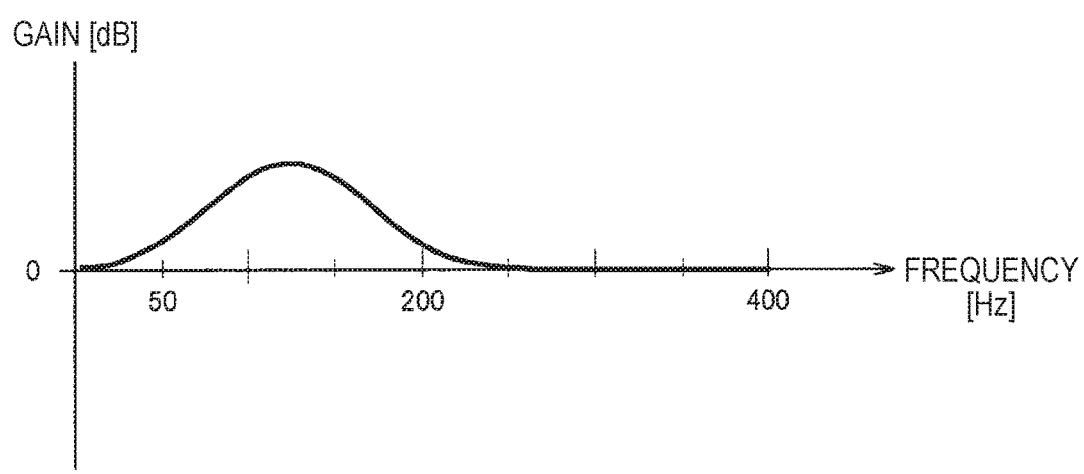
FIG. 11 is an explanatory diagram for describing an example of processing related to modulation of tactile data.
Figure 12:
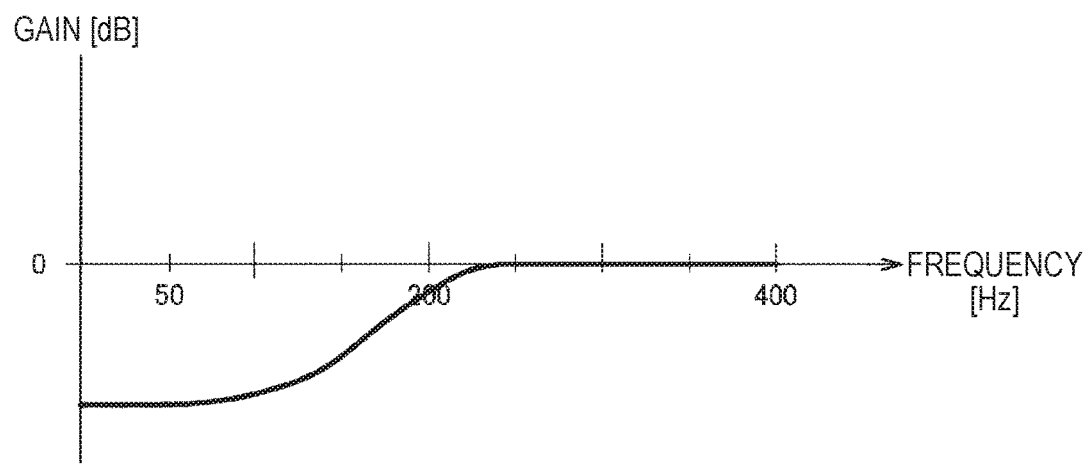
FIG. 12 is an explanatory diagram for describing an example of processing related to modulation of tactile data.
Figure 13:
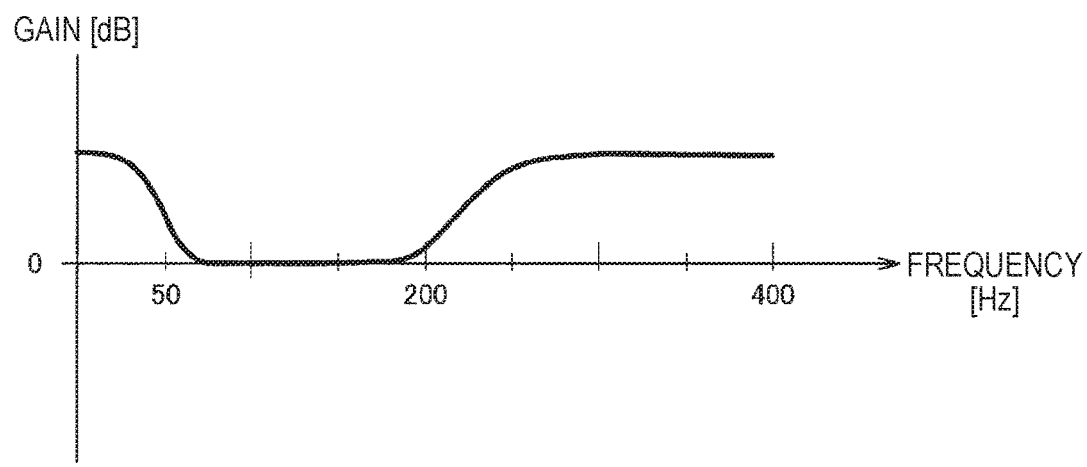
FIG. 13 is an explanatory diagram for describing an example of processing related to modulation of tactile data.
Figure 14:
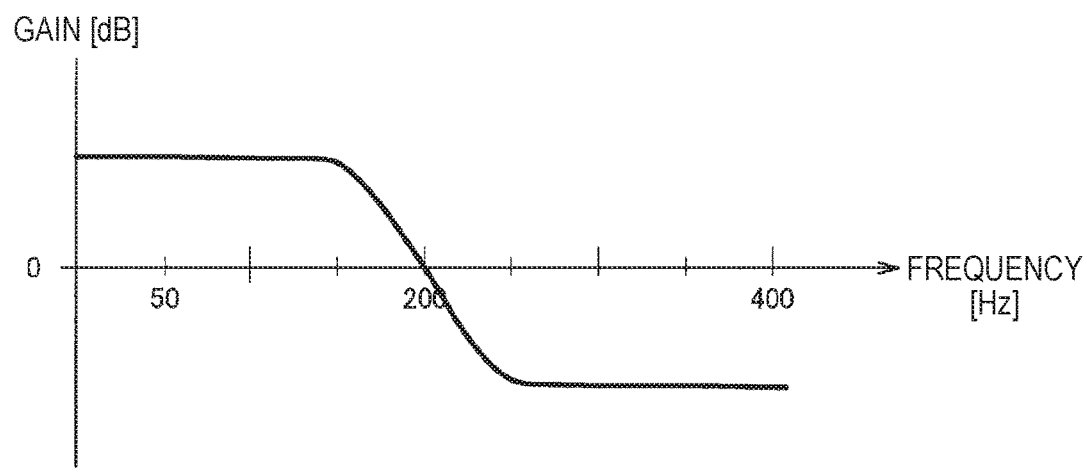
FIG. 14 is an explanatory diagram for describing an example of processing related to modulation of tactile data.

For example, FIG. 9 shows an example of gains applied to respective frequency components in the case of exerting control such that the tactile strength becomes higher in the whole range from the low range to the high range. In addition, FIG. 10 shows an example of gains applied to respective frequency components in the case of exerting control such that the tactile strength in the low range becomes lower. In addition, FIG. 11 shows an example of gains applied to respective frequency components in the case of exerting control such that the tactile strength in the middle range becomes higher. In addition, FIG. 12 shows an example of gains applied to respective frequency components in the case of exerting control such that the tactile strength becomes lower from the low range to the middle range. In addition, FIG. 13 shows an example of gains applied to respective frequency components in the case of exerting control such that the tactile strengths in the low range and the high range become higher. In addition, FIG. 14 shows an example of gains applied to respective frequency components in the case of exerting control such that the tactile strength becomes higher from the low range to the middle range and the tactile strength in the high range becomes lower.

Of course, the examples shown in FIG. 9 to FIG. 14 are merely examples, and are not necessarily limited only to these examples, but contents of modulation processing may be changed appropriately in accordance with various states or situations. For example, the tactile data modulation unit 105 may carry out modulation processing on tactile data such that the contrast of tactile presentation is controlled for each frequency component of the tactile data. Note that a more specific correspondence between various states or situations in accordance with the analysis result of external information and contents of modulation processing to be carried out on tactile data will be described later separately as examples.

Then, the tactile data modulation unit 105 outputs the tactile data after modulation to the output control unit 107.

In addition, the tactile data modulation unit 105 may cause the tactile data after modulation to be stored in the storage unit 15. In this case, the tactile data modulation unit 105 may cause the tactile data after modulation to be stored in the storage unit 15 upon correlating information indicating the analysis result of corresponding external information (that is, information indicating the analysis result of external information used for specifying modulation processing) to the tactile data after modulation, for example. With such a configuration, in the case where the data after modulation has already been stored in the storage unit 15, it is no longer necessary for the tactile data modulation unit 105 to perform modulation of tactile data again.

The output control unit 107 is a component for controlling the operation of the haptics unit 30 on the basis of tactile data. For example, the output control unit 107 may acquire the tactile data after modulation from the tactile data modulation unit 105, and may control the operation of the haptics unit 30 on the basis of the acquired tactile data after modulation. In addition, the output control unit 107 may acquire tactile data (for example, tactile data after modulation) from the tactile data analysis unit 103, and may control the operation of the haptics unit 30 on the basis of the acquired tactile data.

Note that the functional configuration of the information processing system 1 described with reference to FIG. 8 is merely an example, and the functional configuration of the information processing system 1 is not necessarily limited only to the example shown in FIG. 8 as long as it is possible to achieve processing in each of the above-described configurations. As a specific example, two or more components among the information processing device 10, the haptics unit 30, and the external information acquisition device 50 may be configured integrally as described earlier. In addition, as another example, the storage unit 15 may be included in the information processing device 10. In addition, as another example, some components among the respective components of the information processing device 10 may be provided at the outside of the information processing device 10 (for example, a server or the like).

Description has been provided above with reference to FIG. 8 as an example of the functional configuration of the information processing system according to an embodiment of the present disclosure, particularly paying attention to the configuration of the information processing device 10.

2.4. Processing

Figure 15:
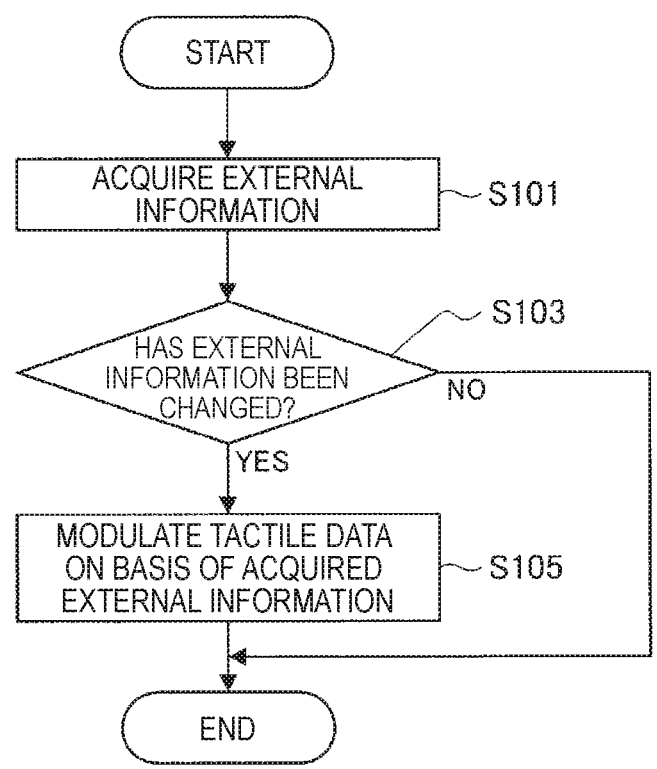
FIG. 15 is a flowchart showing an example of a flow of sequential processing of the information processing system according to the embodiment.

Subsequently, an example of a flow of sequential processing of the information processing system according to an embodiment of the present disclosure will be described with reference to FIG. 15, particularly paying attention to processing related to modulation of tactile data performed by the information processing device 10. FIG. 15 is a flowchart showing an example of a flow of sequential processing of the information processing system according to the present embodiment.

As shown in FIG. 15, the information processing device 10 (the external information analysis unit 101) acquires external information from the external information acquisition device 50 (S101), and analyzes the acquired external information to recognize whether or not the external information (for example, various states or situations such as an external environment or the state of the user) has been changed.

In the case where the external information has been changed (S103, YES), the information processing device 10 modulates the tactile data on the basis of the analysis result of the external information (S105). Specifically, the information processing device 10 (the tactile data analysis unit 103) reads tactile data corresponding to a tactile sense to be presented to the user from a predetermined storage area (for example, the storage unit 15). Next, by carrying out analysis processing on the read tactile data, the information processing device 10 recognizes contents of the tactile data. Then, the information processing device 10 (the tactile data modulation unit 105) determines modulation processing to be carried out on the tactile data on the basis of the analysis result of the external information, and carries out the determined modulation processing on the tactile data to be targeted for modulation. With such control, it is possible for the information processing device 10 to present a tactile sense in accordance with the change in the external information to the user by controlling the operation of the haptics unit 30 on the basis of the tactile data after modulation.

Note that, in the case where the external information has not been changed (S103, NO), the information processing device 10 may not perform modulation of the tactile data.

An example of the flow of sequential processing of the information processing system according to an embodiment of the present disclosure has been described above with reference to FIG. 15, particularly paying attention to the processing related to modulation of tactile data performed by the information processing device 10.

3. EXAMPLES

3.1. Example 1: Example of Control in Accordance with User

Subsequently, examples of an embodiment of the present disclosure will be described. First, as Example 1, an example of control related to modulation of tactile data for reducing the difference in way of feeling a tactile sense between respective users will be described using specific examples.

(With Regard to Sensitivity of Tactile Receptors)

For describing Example 1, first, as a mechanism for a person to feel a tactile sense, a pressure sense, or the like, an example of tactile receptors in the skin and characteristics of sensitivities of the respective tactile receptors will be described with reference to FIG. 16 and FIG. 17.

Figure 16:
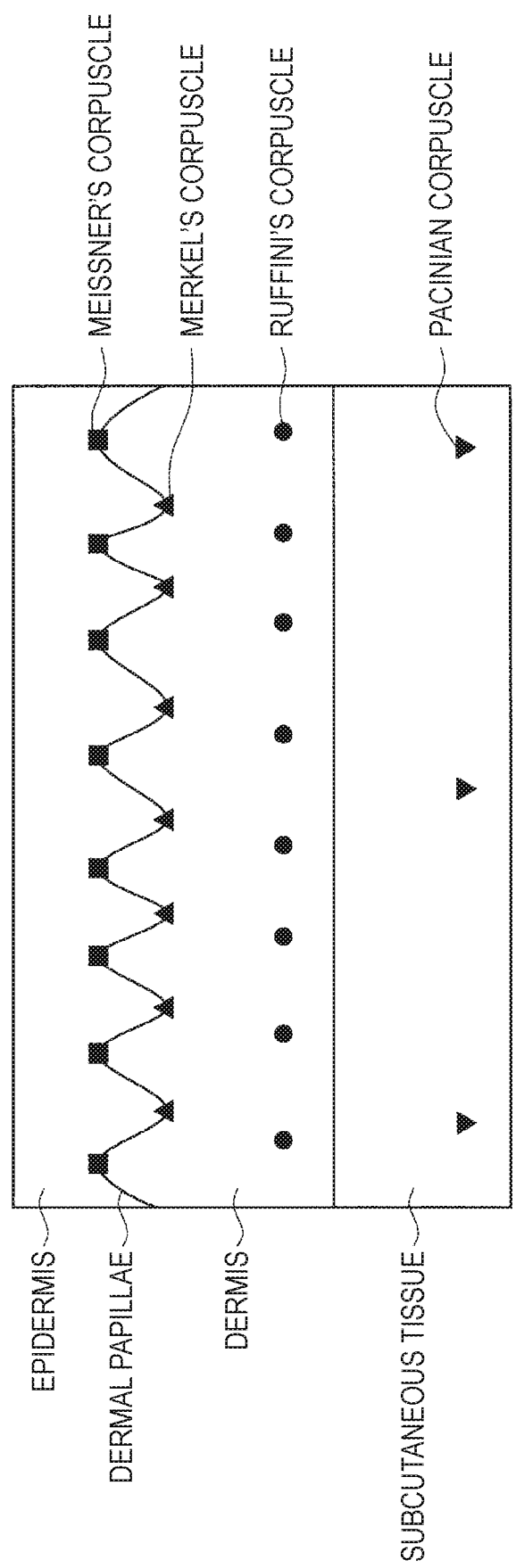
FIG. 16 is an explanatory diagram for describing an example of tactile receptors in the skin and their distribution.
Figure 17:
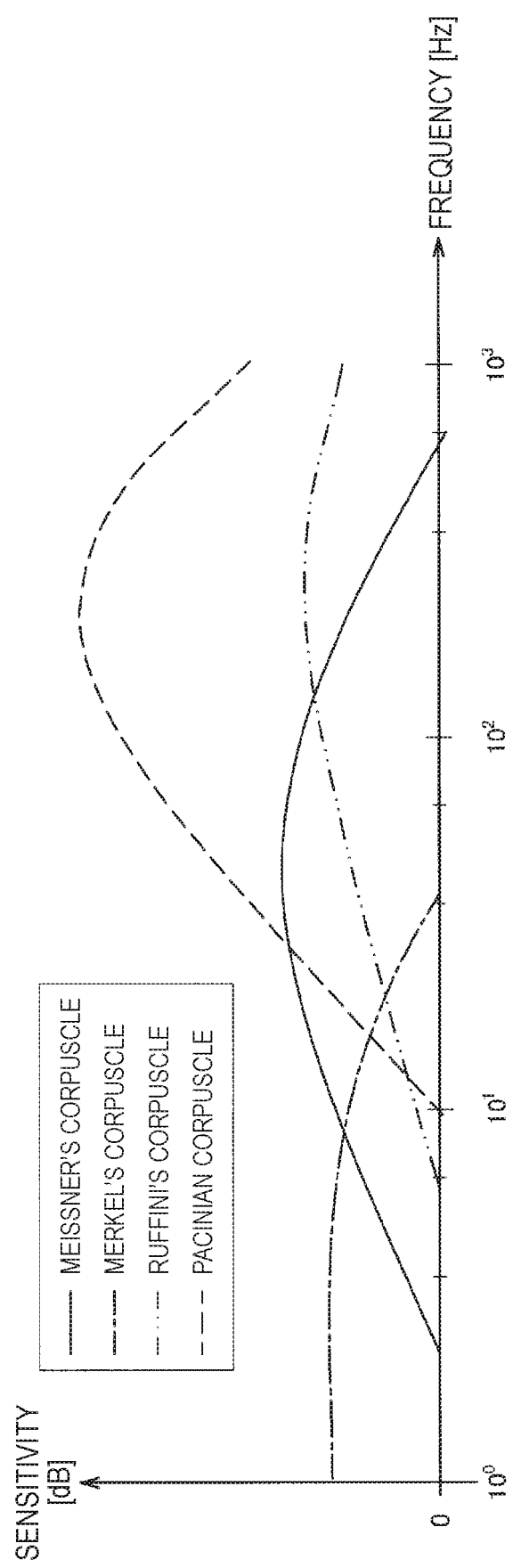
FIG. 17 is an explanatory diagram for describing characteristics of sensitivities of the tactile receptors in the skin.

For example, FIG. 16 is an explanatory diagram for describing an example of tactile receptors in the skin and their distribution. As shown in FIG. 16, the human skin includes the epidermis, dermal papillae, dermis, and subcutaneous tissue in layers in the order from the surface side toward the inside of the body. In addition, as shown in FIG. 16, the tactile receptors in the skin include the Meister's corpuscles, Merkel's corpuscles, Ruffini's corpuscles, and Pacinian corpuscles. The Meissner's corpuscles exist in the dermal papillae. In addition, the Merkel's corpuscles exist in the deepest part of the dermis stratum basale between the dermal papillae. In addition, the Ruffini's corpuscles exist in the deep part of the dermis. In addition, the Pacinian corpuscles exist in the subcutaneous tissue and in the deep layer of the dermis.

It is known that these tactile receptors each vary in frequency characteristics of sensitivity in the case of applying mechanical vibratory stimulation. For example, FIG. 17 is an explanatory diagram for describing sensitivity characteristics of the respective tactile receptors. In FIG. 17, the horizontal axis indicates the frequency, and the vertical axis indicates the sensitivity. As shown in FIG. 17, the Merkel's corpuscle tends to have a higher sensitivity mainly in the low frequency band. In addition, the Meissner's corpuscle tends to have a higher sensitivity mainly in the middle range frequency band. In addition, the Ruffini's corpuscle and Pacinian corpuscle tend to have higher sensitivities mainly from the middle range to the high range frequency band.

By utilizing the sensitivity characteristics of the respective tactile receptors as described above, the information processing device 10 according to Example 1 may modulate tactile data such that the difference in way of feeling a tactile sense in accordance with a change in the state of the user and the difference in way of feeling a tactile sense between users are reduced.

(Example of Control in Accordance with Age)

Figure 18:
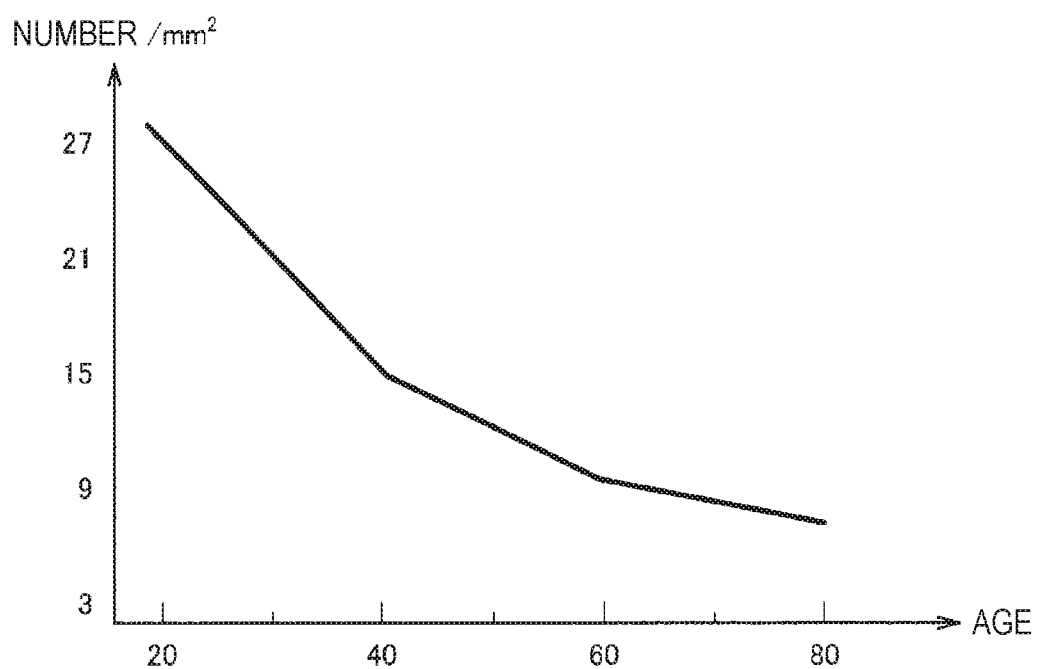
FIG. 18 is an explanatory diagram for describing a mode of an information processing device according to Example 1.

First, an example of the case of controlling a tactile sense to be presented in accordance with the age of the user will be described. For example, FIG. 18 is an explanatory diagram for describing a mode of the information processing device 10 according to Example 1, and is an explanatory diagram for describing an example of the relationship between the age and the Meissner's corpuscles. In FIG. 18, the horizontal axis indicates the age, and the vertical axis indicates the number of Meissner's corpuscles per 1 $mm^2$. As shown in FIG. 18, the number of Meissner's corpuscles tends to decrease with age. In addition, as described earlier, the Meissner's corpuscles are involved in perception of vibrations mainly in the middle range frequency band. That is, the sensitivity concerning perception of vibrations in the middle range frequency band tends to be reduced with an increase of age.

Figure 19:
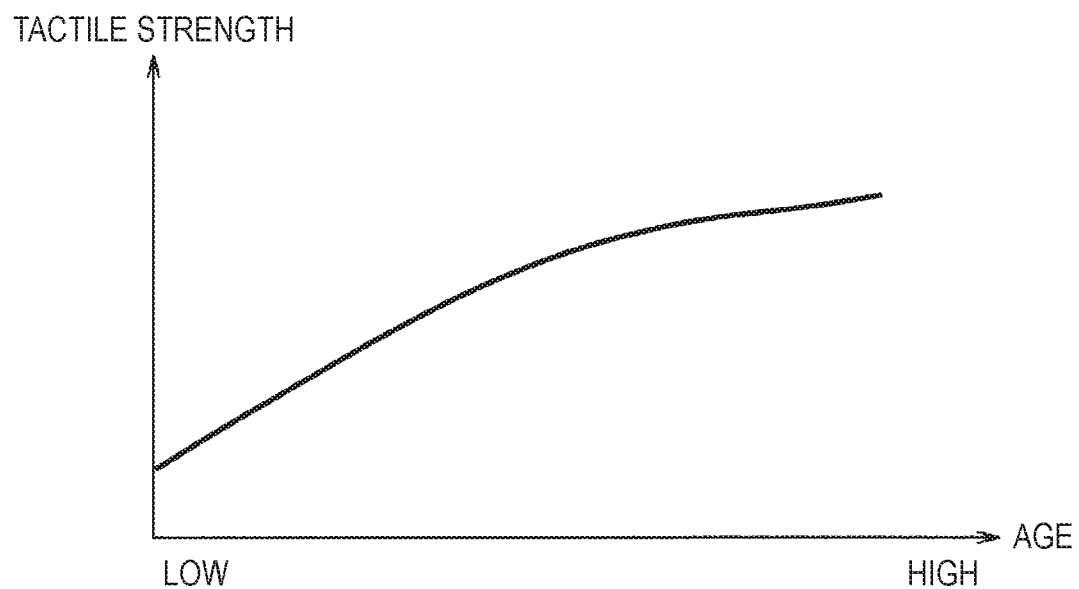
FIG. 19 is an explanatory diagram for describing a mode of an information processing device according to Example 1.

Utilizing the characteristics as described above, for example, the information processing device 10 may modulate tactile data in accordance with the age of the user. For example, FIG. 19 is an explanatory diagram for describing a mode of the information processing device 10 according to Example 1, and shows an example of control related to modulation of tactile data in accordance with the age of the user. In FIG. 19, the horizontal axis indicates the age, and the vertical axis indicates the tactile strength. As shown in FIG. 19, the information processing device 10 may modulate tactile data such that the tactile strength becomes higher as the age of the user is higher, for example. Note that, at this time, the information processing device 10 may control the tactile strength mainly targeting frequency components in the middle range in the tactile data, for example. With such control, it is possible to reduce the difference in way of feeling a tactile sense between users having different ages. That is, the information processing device 10 may modulate tactile data targeting the frequency band corresponding to the ages of users such that an influence upon the tactile sensitivity exerted by the difference in age is corrected.

(Example of Control in Accordance with Sex)

Figure 20:
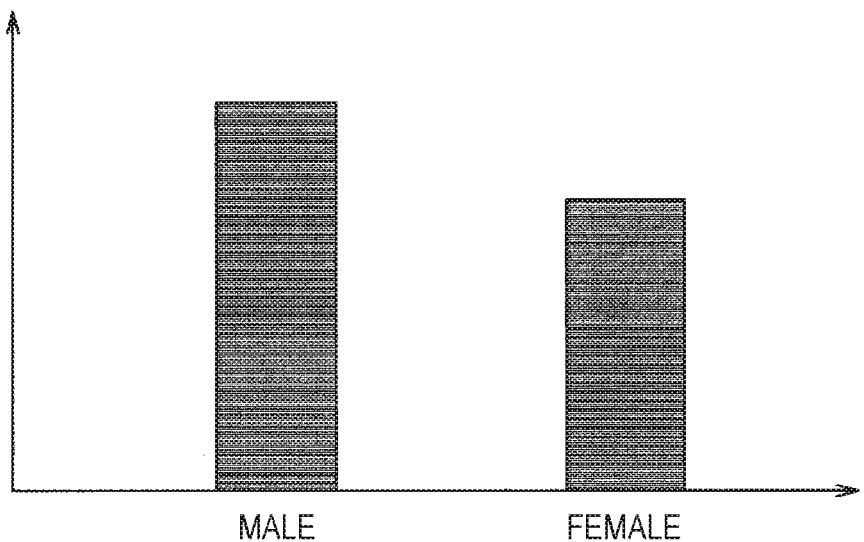
FIG. 20 is an explanatory diagram for describing a mode of an information processing device according to Example 1.

Next, an example of the case of controlling a tactile sense to be presented in accordance with the sex of the user will be described. Specifically, women tend to have a higher tactile sensitivity than men. Utilizing such characteristics, for example, the information processing device 10 may modulate tactile data in accordance with the sex of the user. For example, FIG. 20 is an explanatory diagram for describing a mode of the information processing device 10 according to Example 1, and shows an example of control related to modulation of tactile data in accordance with the sex of the user. FIG. 20 shows an example of tactile strengths in respective cases where the sex of the user is male and female. As shown in FIG. 20, in the case where the sex of the user is female, for example, the information processing device 10 may weaken the tactile strength in the whole range from the low range to the high range. That is, the information processing device 10 may modulate tactile data such that an influence upon the tactile sensitivity exerted by the difference in sex between users is corrected.

(Example of Control in Accordance with Emotion)

Next, an example of the case of controlling a tactile sense to be presented in accordance with the emotion of the user will be described. For example, in the case where the emotion indicates a negative state, such as when one becomes depressed, neurotransmission tends to become dull, and the tactile sensitivity also tends to become dull. In view of such a situation, the information processing device 10 may strengthen the tactile strength in the whole range from the low range to the high range as the user becomes more depressed, for example. That is, the information processing device 10 may modulate tactile data such that an influence upon the tactile sensitivity exerted by a change in the emotion of the user is corrected.

Figure 21:
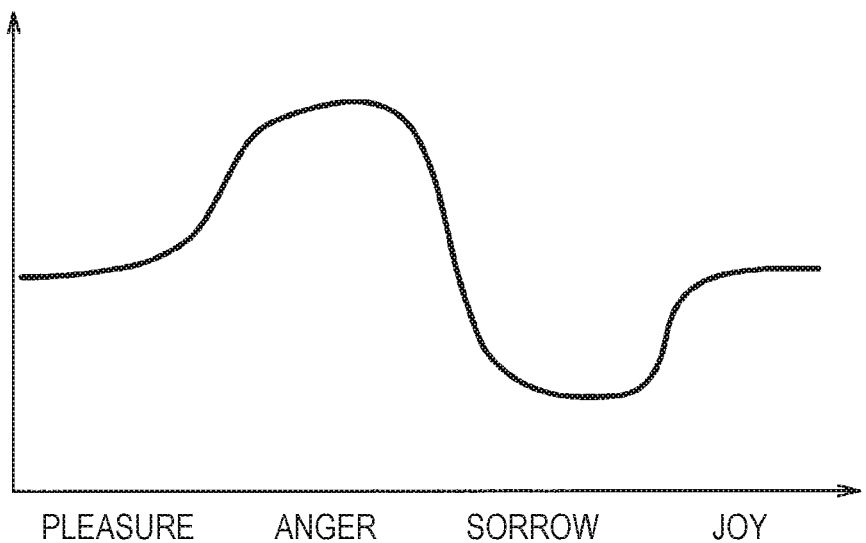
FIG. 21 is an explanatory diagram for describing a mode of an information processing device according to Example 1.

In addition, FIG. 21 is an explanatory diagram for describing a mode of the information processing device 10 according to Example 1, and shows an example of control in accordance with the emotion of the user. As shown in FIG. 21, the information processing device 10 may control the tactile strength of a tactile sense to be presented to the user in accordance with a change in the emotion of the user, such as "pleasure", "anger", "sorrow", or "joy".

(Example of Control in Accordance with Difference in Way of Feeling)

Figure 22:
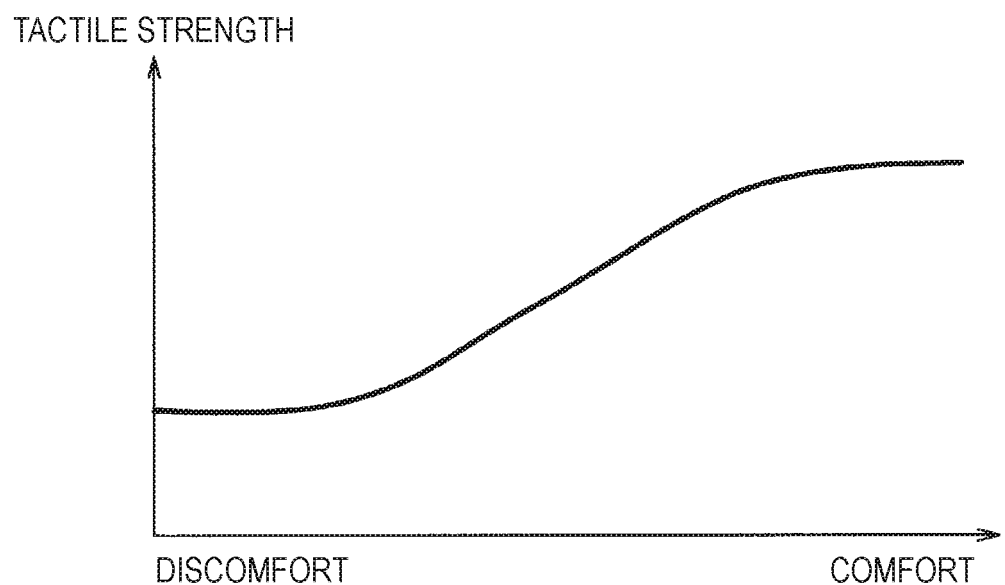
FIG. 22 is an explanatory diagram for describing a mode of an information processing device according to Example 1.

Next, an example of the case of controlling a tactile sense to be presented in accordance with the difference in way of feeling between users will be described. For example, FIG. 22 is an explanatory diagram for describing a mode of the information processing device 10 according to Example 1, and shows an example of control in accordance with the difference in way of feeling between users. In the example shown in FIG. 22, the horizontal axis quantitatively indicates the difference in way of feeling between users, such as "comfort" and "discomfort", and the vertical axis indicates the tactile strength. That is, in the example shown in FIG. 22, the tactile strength of a tactile sense to be presented to the user is controlled in accordance with a detection result of the difference in way of feeling of the user such as "comfort" or "discomfort". More specifically, in the case where it is recognized that the user feels discomfort, the information processing device 10 may weaken the tactile strength of a tactile sense to be presented to the user. In addition, in the case where it is recognized that the user feels comfort, the information processing device 10 may strengthen the tactile strength of a tactile sense to be presented to the user. That is, the information processing device 10 may modulate tactile data such that an influence upon the tactile sensitivity exerted by the difference in way of feeling of the user is corrected.

(Example of Control in Accordance with State of User)

Figure 23:
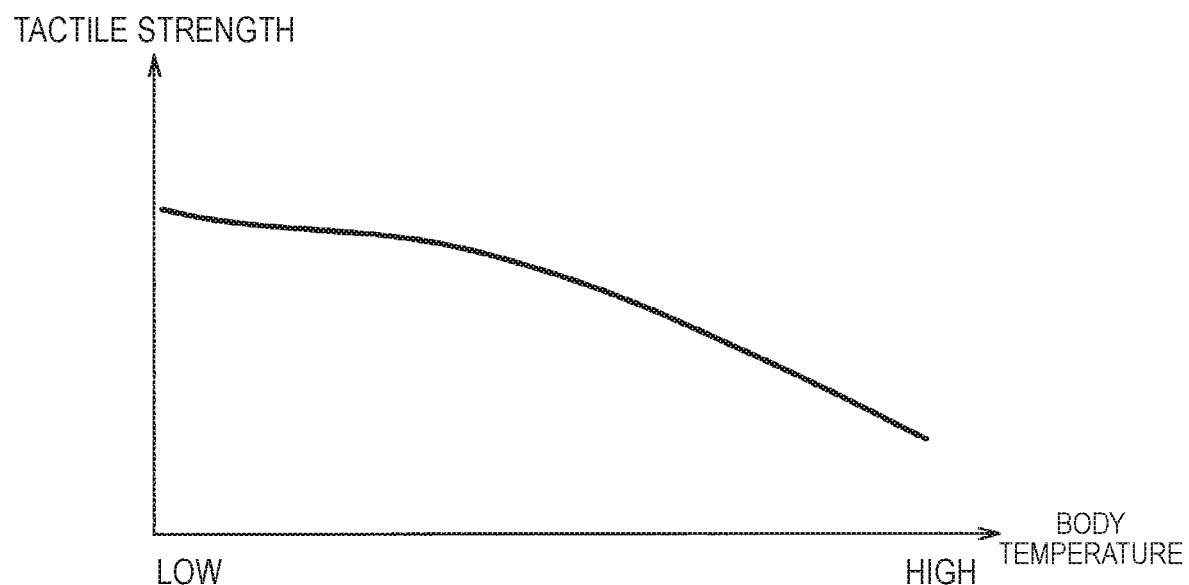
FIG. 23 is an explanatory diagram for describing a mode of an information processing device according to Example 1.

Next, an example of the case of controlling a tactile sense to be presented in accordance with a detection result of various states of the user, such as the body temperature, activity volume, heart rate, or amount of sweat will be described. For example, FIG. 23 is an explanatory diagram for describing a mode of the information processing device 10 according to Example 1, and shows an example of control related to modulation of tactile data in accordance with the body temperature of the user. In the example shown in FIG. 23, the horizontal axis indicates the body temperature, and the vertical axis indicates the tactile strength. More specifically, when the body temperature rises, the Pacinian corpuscles tend to have a higher sensitivity in the subcutaneous tissue. Therefore, the information processing device 10 may weaken the tactile strength from the middle range to the high range in accordance with the rise in the body temperature, for example.

Figure 24:
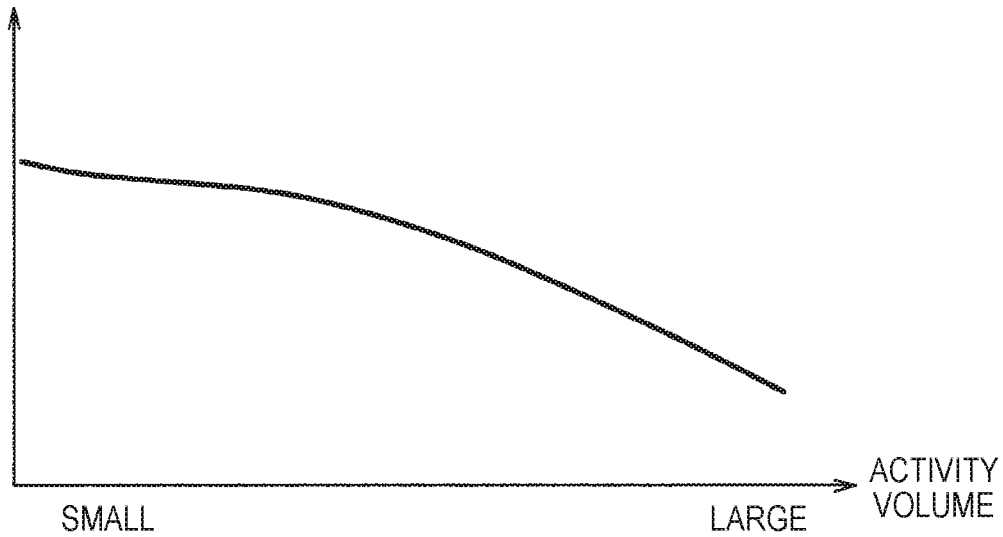
FIG. 24 is an explanatory diagram for describing a mode of an information processing device according to Example 1.

In addition, FIG. 24 is an explanatory diagram for describing a mode of the information processing device 10 according to Example 1, and shows an example of control related to modulation of tactile data in accordance with the activity volume of the user. In the example shown in FIG. 24, the horizontal axis indicates the activity volume, and the vertical axis indicates the tactile strength. Specifically, since the blood flow rate is increased when the activity volume is increased, the body temperature tends to be raised. Therefore, the information processing device 10 may weaken the tactile strength from the middle range to the high range in accordance with the increase in the activity volume of the user, similarly to the case where the body temperature has been raised. That is, targeting a frequency band that corresponds to the body temperature of the user, the information processing device 10 may modulate tactile data such that an influence upon the tactile sensitivity exerted by a change in the body temperature is corrected.

Figure 25:
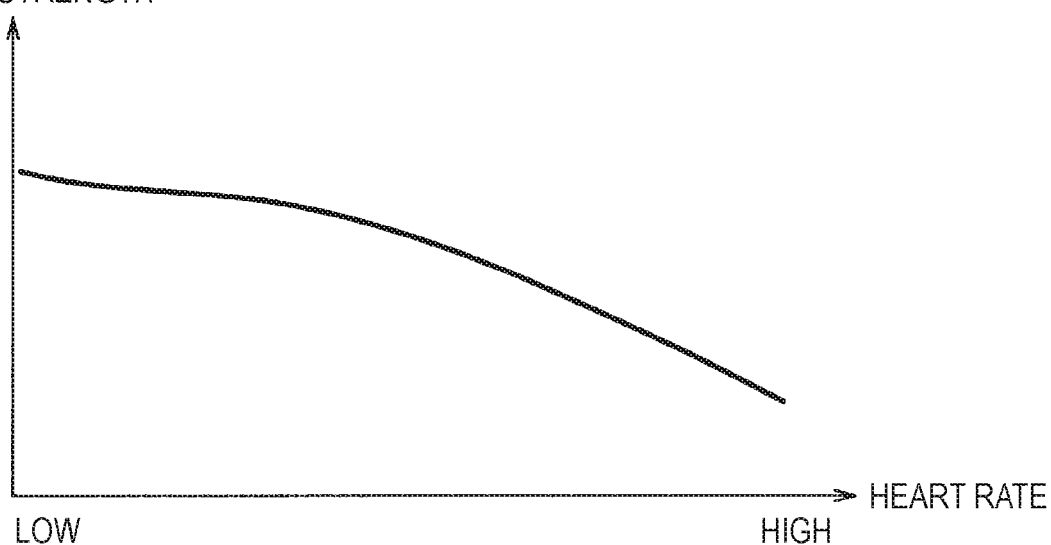
FIG. 25 is an explanatory diagram for describing a mode of an information processing device according to Example 1.

In addition, FIG. 25 is an explanatory diagram for describing a mode of the information processing device 10 according to Example 1, and shows an example of control related to modulation of tactile data in accordance with the heart rate of the user. In the example shown in FIG. 25, the horizontal axis indicates the heart rate, and the vertical axis indicates the tactile strength. Specifically, since the blood flow rate is increased when the heart rate is raised, the body temperature tends to be raised. Therefore, the information processing device 10 may weaken the tactile strength from the middle range to the high range in accordance with an increase in the heart rate of the user, similarly to the case where the body temperature has been raised. That is, targeting a frequency band corresponding to the heart rate of the user, the information processing device 10 may modulate tactile data such that an influence upon the tactile sensitivity exerted by the change in the heart rate is corrected.

Figure 26:
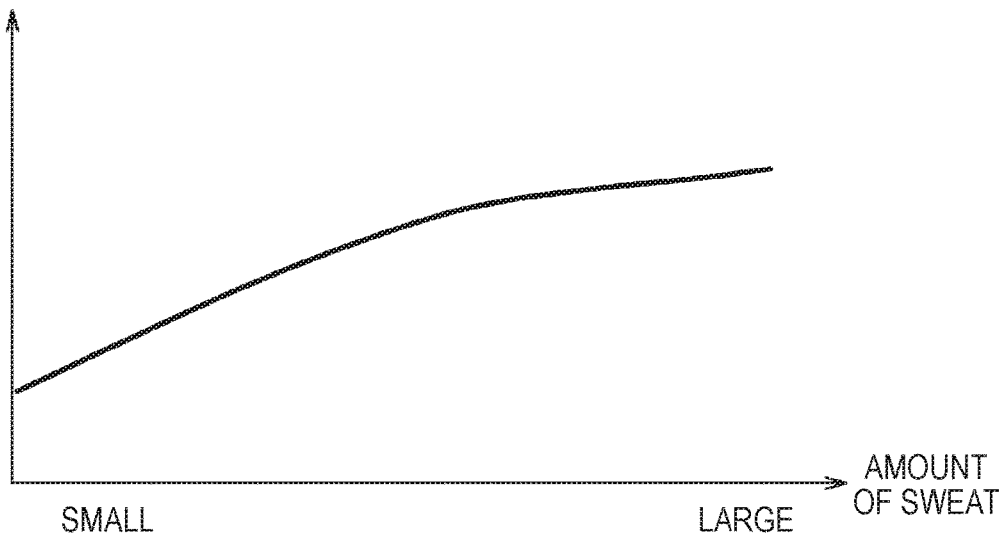
FIG. 26 is an explanatory diagram for describing a mode of an information processing device according to Example 1.

In addition, FIG. 26 is an explanatory diagram for describing a mode of the information processing device 10 according to Example 1, and shows an example of control related to modulation of tactile data in accordance with the amount of sweat of the user. In the example shown in FIG. 26, the horizontal axis indicates the amount of sweat, and the vertical axis indicates the tactile strength. Specifically, when the amount of sweat is increased, the sensitivity of perceiving a tactile sense tends to become dull in the high range frequency band. Therefore, the information processing device 10 may strengthen the tactile strength in the high range in accordance with an increase in the amount of sweat, for example. That is, targeting a frequency band corresponding to the amount of sweat of the user, the information processing device 10 may modulate tactile data such that an influence upon the tactile sensitivity exerted by the change in the amount of sweat is corrected.

Note that, in the case of modulating tactile data on the basis of dynamically changing information such as the above-described state of the user, the information processing device 10 may control timing of control related to the modulation. For example, under such a situation where the state is changed frequently, the information processing device 10 may temporarily stop control related to modulation of tactile data. In this case, for example, after the state becomes stable, the information processing device 10 may modulate tactile data in accordance with the state after becoming stable. In addition, as another example, after a certain time has elapsed since the state is changed, the information processing device 10 may modulate tactile data in accordance with the state after the change. Note that the present control is not limited to the example described above as Example 1, but also may be applied to an example which will be described later as Example 2.

(Example of Control Based on Plurality of Pieces of External Information)

Next, an example of the case of controlling a tactile sense to be presented on the basis of a plurality of pieces of external information will be described. The information processing device 10 may control a tactile sense on the basis of a plurality of pieces of external information (that is, in accordance with a plurality of states or situations) among pieces of external information (context information) indicating the aforementioned various states or situations. In this case, the information processing device 10 may perform weighting (that is, may set priorities) for the targeted plurality of pieces of external information (in other words, various states or situations), and may modulate tactile data in accordance with the placed weights. In addition, at this time, the information processing device 10 may mix modulation methods corresponding to the respective pieces of external information in accordance with the weights set for the pieces of external information. Note that the present control is not limited to the example described above as Example 1, but also may be applied to an example which will be described later as Example 2.

(Method of Detecting Difference in Characteristics Between Users)

Subsequently, an example of a mechanism for detecting a difference in characteristics between users will be described. As described earlier, the way of feeling a tactile sense (for example, pleasant, unpleasant, or the like) may vary between individuals. In view of such a situation, the information processing device 10 may be provided with a mechanism for recognizing the way of feeling a tactile sense (for example, a preference for a tactile sense to be presented, or the like) of each user.

As a specific example, the information processing device 10 may recognize vibrations that a user prefers from an application installed in a terminal (or the information processing device 10 itself) that the target user uses. In addition, as another example, on the basis of a music listening history, music data held in the terminal, or the like, the information processing device 10 may determine the genre of the music, and may recognize vibrations that the user prefers on the basis of the determined genre of the music.

In addition, the information processing device 10 may present a plurality of types of vibrations to the user, and may cause the user to select favorite vibrations from among presented vibrations to recognize the vibrations that the user prefers. As a specific example, the information processing device 10 may present one or more of the above-described questions for recognizing a preference of the user at the initial setting, and in accordance with a response from the user (that is, a result of selection made by the user), may recognize the vibrations that the user prefers.

In addition, the information processing device 10 may display the strength of vibrations or the like with numeric values, indicators, or the like for presentation to the user. With such control, it is possible for the user to visually recognize the strength of vibrations or the like. In addition, along with such control, the information processing device 10 may be configured to be capable of changing the strength of vibrations or the like on the basis of an instruction from the user.

An example of control related to modulation of tactile data for reducing the difference in way of feeling a tactile sense between respective users has been described above as Example 1 of an embodiment of the present disclosure, using specific examples. With the control as described above, it is possible for the information processing device 10 to exert control such that the difference in way of feeling a tactile sense associated with a change in the state of the user and the difference in way of feeling a tactile sense between different users are reduced. Therefore, it is possible for the information processing device 10 to reproduce a more realistic tactile sense.

3.2. Example 2: Example of Control in Accordance with External Environment

Subsequently, an example of control related to modulation of tactile data for reducing a change in the way of feeling a tactile sense associated with a change in the state of an external environment will be described as Example 2 of an embodiment of the present disclosure, using specific examples.

(Example of Control in Accordance with Brightness of External Environment)

Figure 27:
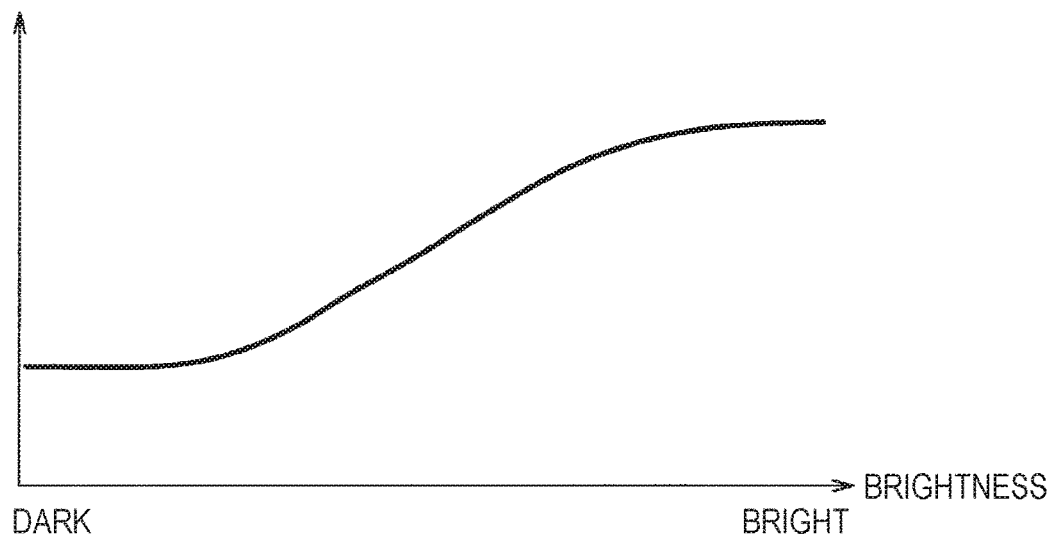
FIG. 27 is an explanatory diagram for describing a mode of an information processing device according to Example 2.

First, an example of the case of controlling a tactile sense to be presented in accordance with the brightness of the external environment will be described. For example, FIG. 27 is an explanatory diagram for describing a mode of the information processing device 10 according to Example 2, and shows an example of control related to modulation of tactile data in accordance with the brightness of the external environment. In the example shown in FIG. 27, the horizontal axis indicates the brightness of the external environment, and the vertical axis indicates the tactile strength. More specifically, when the surrounding environment (that is, external environment) becomes darker, the user tends to have a higher tactile sensitivity. Therefore, the information processing device 10 may weaken the tactile strength as the brightness of the external environment becomes darker, for example. Note that, at this time, the information processing device 10 may weaken the tactile strength in the whole range from the low range to the high range, or may weaken the tactile strength only for some frequency bands. That is, the information processing device 10 may modulate tactile data such that an influence upon the tactile sensitivity exerted by the difference in brightness of the external environment is corrected.

(Example of Control in Accordance with Noise in External Environment)

Figure 28:
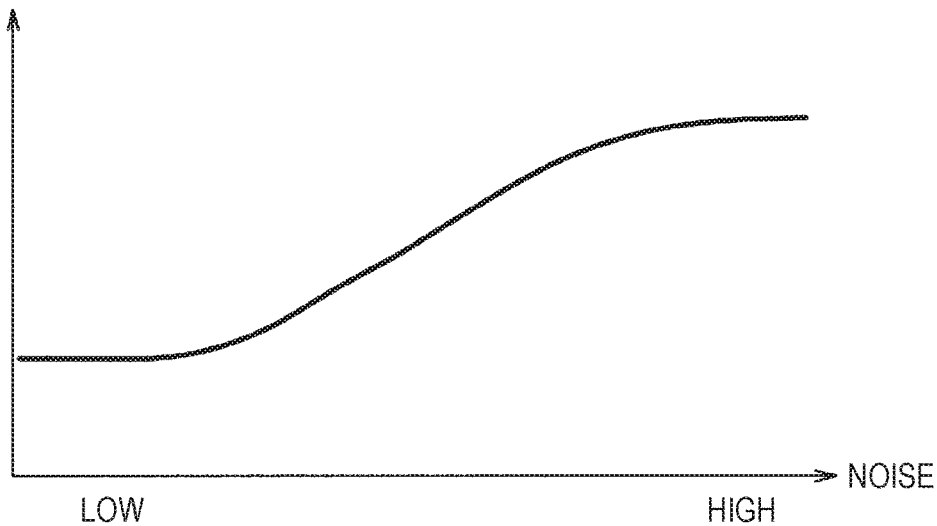
FIG. 28 is an explanatory diagram for describing a mode of an information processing device according to Example 2.

Next, an example of the case of controlling a tactile sense to be presented in accordance with noise (sound) in an external environment will be described. For example, FIG. 28 is an explanatory diagram for describing a mode of the information processing device 10 according to Example 2, and shows an example of control related to modulation of tactile data in accordance with noise in the external environment. In the example shown in FIG. 28, the horizontal axis indicates the magnitude of noise level in the external environment, and the vertical axis indicates the tactile strength. More specifically, by the influence of noise, the user tends to have a lower sensitivity to vibrations of a component in a frequency band identical to or in the vicinity of the frequency band of the noise. Therefore, in the case where a low range component is included in the noise, for example, the information processing device 10 may strengthen the tactile strength in the low range. In addition, in the case where a middle range component is included in the noise, the information processing device 10 may strengthen the tactile strength in the middle range. Similarly, in the case where a high range component is included in the noise, the information processing device 10 may strengthen the tactile strength in the high range. That is, targeting a frequency band in accordance with a frequency component included in sound in the external environment, the information processing device 10 may modulate tactile data such that an influence upon the tactile sensitivity exerted by the sound is corrected.

(Example of Control in Accordance with Temperature of External Environment)

Figure 29:
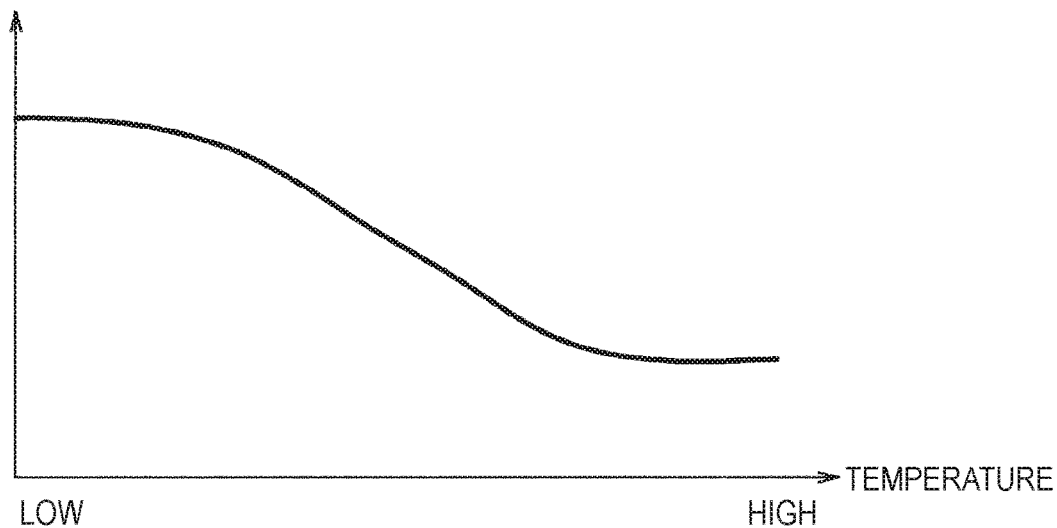
FIG. 29 is an explanatory diagram for describing a mode of an information processing device according to Example 2.

Next, an example of the case of controlling a tactile sense to be presented in accordance with the temperature of an external environment will be described. For example, FIG. 29 is an explanatory diagram for describing a mode of the information processing device 10 according to Example 2, and shows an example of control related to modulation of tactile data in accordance with the temperature (air temperature) of the external environment. In the example shown in FIG. 29, the horizontal axis indicates the air temperature, and the vertical axis indicates the tactile strength. More specifically, since the body temperature drops in association with a drop in air temperature, the user tends to have a lower tactile sensitivity.

Note that, as described earlier, tactile receptors (that is, the Meister's corpuscles, Merkel's corpuscles, Ruffini's corpuscles, and Pacinian corpuscles) having different characteristics exist in the respective layers of the epidermis, dermal papillae, dermis, and subcutaneous tissue that form the skin. Therefore, in accordance with a change in temperature (body temperature) in each of the epidermis, dermal papillae, dermis, and subcutaneous tissue, the way of feeling a tactile sense will also be changed.

Specifically, when the air temperature drops, the body temperature of the skin of the user drops in the order from the layer closer to the surface (that is, in the order of the epidermis, dermal papillae, dermis, and subcutaneous tissue). More specifically, the temperature of the epidermis drops first, and neurotransmission of the Meissner's corpuscles becomes dull (that is, the sensitivity is reduced). Therefore, the information processing device 10 may strengthen the tactile strength in the middle range. Next, when the temperature drops down to the dermal papillae, neurotransmission of the Merkel's corpuscles becomes dull. Therefore, the information processing device 10 may strengthen the tactile strength further in the low range. Next, when the temperature drops down to the dermis, neurotransmission of the Ruffini's corpuscles becomes dull. Therefore, the information processing device 10 may strengthen the tactile strength further from the middle range to the high range. In addition, when the temperature drops down to the subcutaneous tissue, neurotransmission of the Pacinian corpuscles becomes dull. Therefore, the information processing device 10 may strengthen the tactile strength further in the high range. That is, targeting a frequency band in accordance with the temperature of the external environment, the information processing device 10 may modulate tactile data such that an influence upon the tactile sensitivity exerted by the difference in temperature is corrected. In addition, targeting a frequency band corresponding to at least any layer among the epidermis, dermal papillae, dermis, and subcutaneous tissue that form the skin of the user, the information processing device 10 may modulate tactile data such that an influence upon the tactile sensitivity exerted by the difference in temperature between the layers is corrected.

An example of control related to modulation of tactile data for reducing a change in the way of feeling a tactile sense associated with a change in the state of the external environment has been described above as Example 2 of an embodiment of the present disclosure, using specific examples. With the control as described above, it is possible for the information processing device 10 to exert control such that the difference in way of feeling a tactile sense associated with a change in the state of the external environment is reduced. Therefore, it is possible for the information processing device 10 to reproduce a more realistic tactile sense.

3.3. Example 3: Other Control Examples

Subsequently, an example of other controls different from Examples 1 and 2 described earlier will be described as Example 3 of an embodiment of the present disclosure.
(Example of Control in Accordance with Placed Part)

Figure 30:
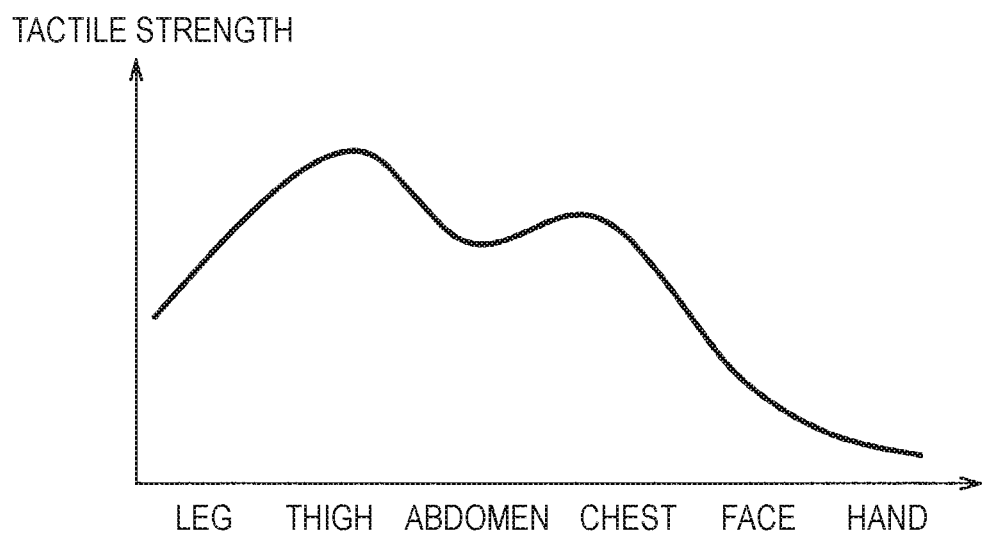
FIG. 30 is an explanatory diagram for describing a mode of an information processing device according to Example 3.

First, an example of the case of controlling a tactile sense to be presented in accordance with a part on which the haptics unit 30 is placed will be described. Specifically, the way of feeling a tactile sense of the user may vary in accordance with the part. That is, even if the haptics unit 30 presents a tactile sense at a predetermined tactile strength, the way of feeling the presented tactile sense may vary in accordance with the part on which the haptics unit 30 is placed. Therefore, in accordance with the part on which the haptics unit 30 is placed, the information processing device 10 may control the tactile strength of the tactile sense to be presented via the haptics unit 30. For example, FIG. 30 is an explanatory diagram for describing a mode of the information processing device 10 according to Example 3, and shows an example of control related to modulation of tactile data in accordance with the part on which the haptics unit 30 is placed. FIG. 30 shows an example of tactile strengths in the leg, thigh, abdomen, chest, face, and hand, respectively, as an example of the part on which the haptics unit 30 is placed.
(Example of Control in Accordance with Placement Pressure)

Next, an example of the case of controlling a tactile sense to be presented in accordance with a placement pressure of the haptics unit 30 will be described. Specifically, even under a situation where the haptics unit 30 is placed on a predetermined part, the way of feeling a tactile sense of the user may vary in accordance with the difference in placement pressure of the haptics unit 30 (for example, whether or not the haptics unit 30 is placed to be brought into closer contact). Therefore, the information processing device 10 may control the tactile strength of a tactile sense to be presented via the haptics unit 30 in accordance with the placement pressure of the haptics unit 30.

Figure 31:
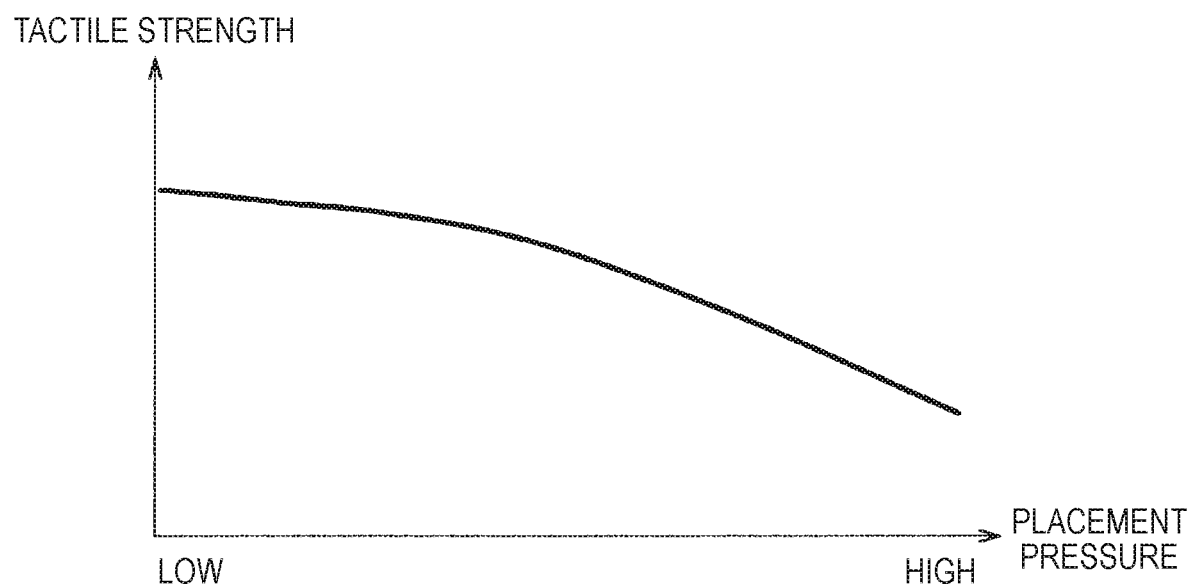
FIG. 31 is an explanatory diagram for describing a mode of an information processing device according to Example 3.

For example, FIG. 31 is an explanatory diagram for describing a mode of the information processing device 10 according to Example 3, and shows an example of control related to modulation of tactile data in accordance with the placement pressure of the haptics unit 30. In the example shown in FIG. 31, the horizontal axis indicates the magnitude of placement pressure, and the vertical axis indicates the tactile strength. More specifically, as the placement pressure of the haptics unit 30 is higher, the haptics unit 30 is brought into closer contact with a part of the user. Therefore, the user tends to be more likely to feel a tactile sense presented by the haptics unit 30 than in the case where the placement pressure of the haptics unit 30 is low. Therefore, the information processing device 10 may weaken the tactile strength as the placement pressure of the haptics unit 30 becomes higher.

An example of other controls different from Examples 1 and 2 described earlier has been described above as Example 3 of an embodiment of the present disclosure.

4. HARDWARE CONFIGURATION

Figure 32:
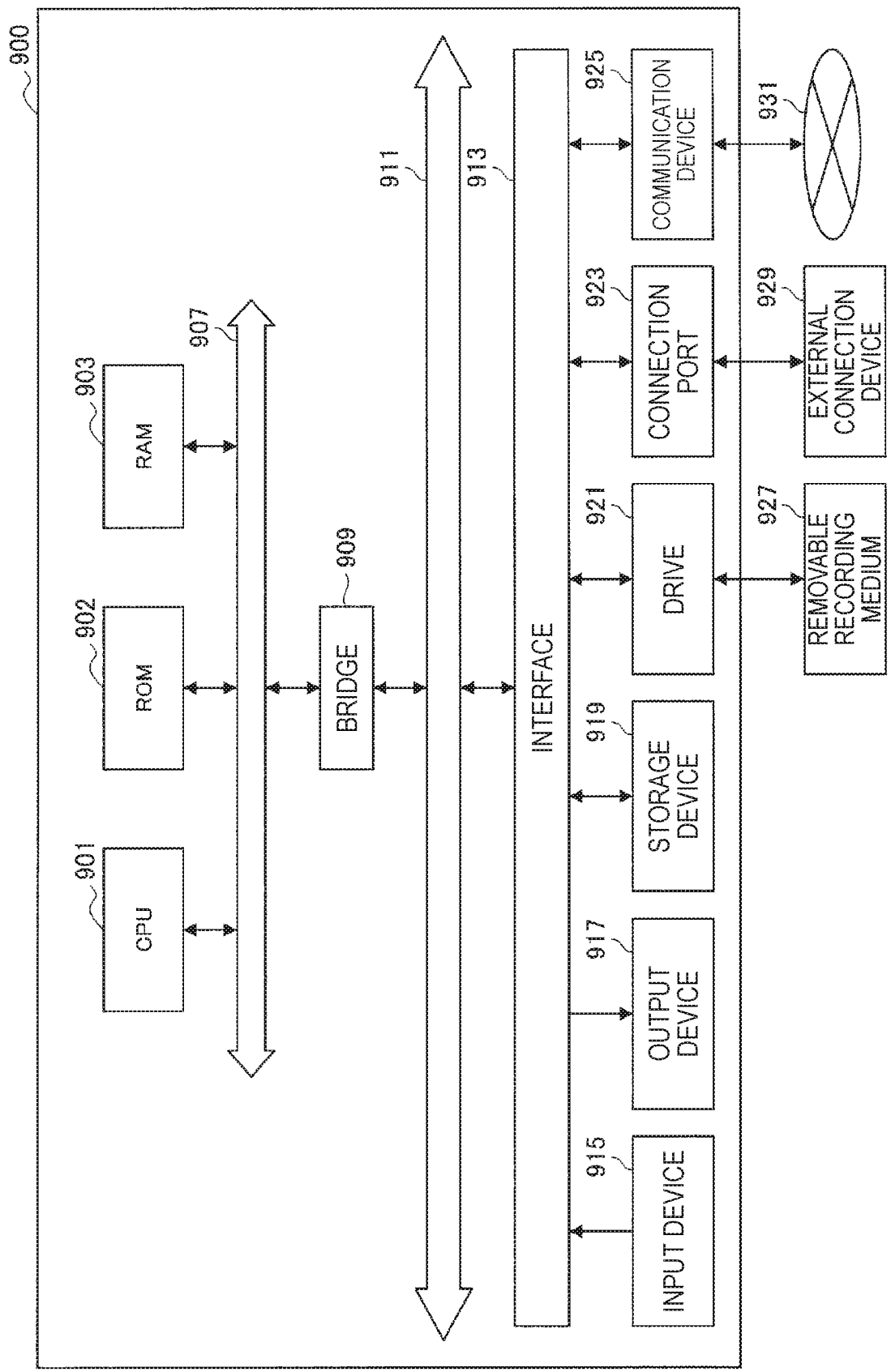
FIG. 32 is a functional block diagram showing a configuration example of a hardware configuration of an information processing device according to an embodiment of the present disclosure.

Next, like the information processing device 10 described above, a hardware configuration of an information processing device 900 included in the information processing system 1 according to the present embodiment will be described in detail with reference to FIG. 32. FIG. 32 is a function block diagram illustrating a configuration example of the hardware configuration of the information processing device 900 included in the information processing system 1 according to the present embodiment of the present disclosure.

The information processing device 900 included in the information processing system 1 according to the present embodiment mainly includes a CPU 901, a ROM 903, and a RAM 905. Furthermore, the information processing device 900 also includes a host bus 907, a bridge 909, an external bus 911, an interface 913, an input device 915, an output device 917, a storage device 919, a drive 921, a connection port 923, and a communication device 925.

The CPU 901 serves as an arithmetic processing device and a control device, and controls the overall operation or a part of the operation of the information processing device 900 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 including an internal bus such as a CPU bus or the like. Note that the external information analysis unit 101, the tactile data analysis unit 103, the tactile data modulation unit 105, and the output control unit 107 described earlier with reference to FIG. 8 may be implemented by the CPU 901, for example.

The host bus 907 is connected to the external bus 911 such as a PCI (Peripheral Component Interconnect/Interface) bus via the bridge 909. Additionally, the input device 915, the output device 917, the storage device 919, the drive 921, the connection port 923, and the communication device 925 are connected to the external bus 911 via the interface 913.

The input device 915 is an operation mechanism operated by a user, such as a mouse, a keyboard, a touch panel, buttons, a switch, a lever, or a pedal. Also, the input device 915 may be a remote control mechanism (a so-called remote control) using, for example, infrared light or other radio waves, or may be an external connection device 929 such as a mobile phone or a PDA conforming to the operation of the information processing device 900. Furthermore, the input device 915 generates an input signal based on, for example, information which is input by a user with the above operation mechanism, and includes an input control circuit for outputting the input signal to the CPU 901. The user of the information processing device 900 can input various data to the information processing device 900 and can instruct the information processing device 900 to perform processing by operating the input device 915.

The output device 917 includes a device capable of visually or audibly notifying acquired information to a user. Examples of such device include display devices such as a CRT display device, a liquid crystal display device, a plasma display device, an EL display device and lamps, audio output devices such as a speaker and a headphone, a printer, and the like. For example, the output device 917 outputs a result obtained by various processes performed by the information processing device 900. More specifically, the display device displays, in the form of texts or images, a result obtained by various processes performed by the information processing device 900. On the other hand, the audio output device converts an audio signal including reproduced audio data and sound data into an analog signal, and outputs the analog signal.

The storage device 919 is a device for storing data configured as an example of a storage unit of the information processing device 900. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, and various data.

The drive 921 is a reader/writer for recording medium, and is embedded in the information processing device 900 or attached externally thereto. The drive 921 reads information recorded in the attached removable recording medium 927 such as a magnetic disk, an optical disc, a magneto-optical disk, or a semiconductor memory, and outputs the read information to the RAM 905. Furthermore, the drive 921 can write record in the attached removable recording medium 927 such as a magnetic disk, an optical disc, a magneto-optical disk, or a semiconductor memory. The removable recording medium 927 is, for example, a DVD medium, an HD-DVD medium, or a Blu-ray (a registered trademark) medium. In addition, the removable recording medium 927 may be a CompactFlash (CF: a registered trademark), a flash memory, an SD memory card (Secure Digital Memory Card), or the like.

Alternatively, the removable recording medium 927 may be, for example, an IC card (Integrated Circuit Card) equipped with a non-contact IC chip or an electronic appliance. Note that the storage unit 15 described earlier with reference to FIG. 8 may be implemented by at least any of the RAM 905, the storage device 919, and the removable recording medium 927, for example.

The connection port 923 is a port for allowing devices to directly connect to the information processing device 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (a registered trademark) (High-Definition Multimedia Interface) port, and the like. By the external connection device 929 connecting to this connection port 923, the information processing device 900 directly obtains various types of data from the external connection device 929 and provides various types of data to the external connection device 929.

The communication device 925 is a communication interface including, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 includes a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing device 900 included in the information processing system 1 according to the embodiment of the present disclosure has been shown. Each of the structural elements described above may be configured using a general-purpose material, or may be implemented by hardware dedicated to the function of each structural element. Accordingly, the hardware configuration to be used can be changed as appropriate according to the technical level at the time of carrying out the present embodiment. Note that, although not shown in FIG. 32, for example, it naturally includes various configurations corresponding to the information processing device 900 included in the information processing system 1 according to the present embodiment.

Note that it is also possible to develop a computer program for realizing the respective functions of the information processing device 900 included in the information processing system 1 according to the present embodiment as discussed above, and implement the computer program in a personal computer or the like. In addition, a computer-readable recording medium storing such a computer program may also be provided. The recording medium may be a magnetic disk, an optical disc, a magneto-optical disk, or flash memory, for example. Furthermore, the above computer program may also be delivered via a network, for example, without using a recording medium. In addition, the number of computers causing the computer program to be executed is not particularly limited. For example, the computer program may be executed in cooperation of a plurality of computers (e.g., a plurality of servers or the like). Note that a single computer or a plurality of cooperating computers is also referred to as "computer system."

5. CONCLUSION

As described above, the information processing device 10 according to an embodiment of the present disclosure modulates tactile data (for example, a control signal) for driving the haptics unit 30 in accordance with user-related external information (for example, information concerning the state or attribute of the user, or the like). Accordingly, it is possible for the information processing device 10 to exert control such that the difference in way of feeling a tactile sense associated with a change in the state of the user and the difference in way of feeling a tactile sense between different users are reduced. That is, it is possible for the information processing device 10 to reproduce a more realistic tactile sense.

In addition, the information processing device 10 according to an embodiment of the present disclosure modulates the tactile data for driving the haptics unit 30 in accordance with external information concerning the state or situation of the external environment. Accordingly, it is possible for the information processing device 10 to exert control such that the difference in way of feeling a tactile sense associated with a change in the state of the external environment is reduced. That is, it is possible for the information processing device 10 to reproduce a more realistic tactile sense.

Note that, in the above-described examples, description has been given mainly paying attention to the case of presenting a tactile sense, whilst the same applies to the case of presenting a sense such as a force sense to the body surface such as the skin. That is, with the information processing device 10 according to an embodiment of the present disclosure, it is possible to reproduce more realistic haptics (for example, a tactile sense or a force sense).

The preferred embodiment (s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device including:

an acquisition unit configured to acquire context information concerning a state or a situation of an external environment or context information concerning a user; and a modulation unit configured to modulate a control signal for controlling a haptics unit for presenting haptics to a predetermined part of the user on the basis of the context information having been acquired.

(2)

The information processing device according to (1), in which targeting a frequency band in accordance with the context information having been acquired, the modulation unit modulates the control signal.

(3)

The information processing device according to (2), in which the context information includes information concerning an age of the user, and targeting a frequency band corresponding to the age, the modulation unit modulates the control signal such that an influence exerted by a difference in the age is corrected.

(4)

The information processing device according to (1) or (2), in which the context information includes information concerning a sex of the user, and the modulation unit modulates the control signal such that an influence exerted by a difference in the sex is corrected.

(5)

The information processing device according to (1) or (2), in which the context information includes information concerning a sensing result of an emotion of the user, and in a case where the sensing result of the emotion indicates a negative state, the modulation unit modulates the control signal such that an influence exerted by a change in haptics presented to the user by the haptics unit is corrected.

(6)

The information processing device according to (2), in which the context information includes information concerning a body temperature of the user, and targeting a frequency band corresponding to the body temperature, the modulation unit modulates the control signal such that an influence exerted by a change in the body temperature is corrected.

(7)

The information processing device according to (2), in which the context information includes information concerning an activity volume of the user, and targeting a frequency band corresponding to the activity volume, the modulation unit modulates the control signal such that an influence exerted by a change in the activity volume is corrected.

(8)

The information processing device according to (2), in which the context information includes information concerning a heart rate of the user, and targeting a frequency band corresponding to the heart rate, the modulation unit modulates the control signal such that an influence exerted by a change in the heart rate is corrected.

(9)

The information processing device according to (2), in which the context information includes information concerning an amount of sweat of the user, and targeting a frequency band corresponding to the amount of sweat, the modulation unit modulates the control signal such that an influence exerted by a change in the amount of sweat is corrected.

(10)

The information processing device according to (1) or (2), in which the context information includes information concerning brightness of the external environment, and the modulation unit modulates the control signal such that an influence exerted by a difference in the brightness is corrected.

(11)

The information processing device according to (2), in which the context information includes information based on a sound collection result of sound in the external environment, and targeting the frequency band in accordance with a frequency component included in the sound, the modulation unit modulates the control signal.

(12)

The information processing device according to (1) or (2), in which the context information includes information concerning a temperature of the external environment, and the modulation unit modulates the control signal such that an influence exerted by a difference in the temperature is corrected.

(13)

The information processing device according to (2), in which the context information includes information concerning a temperature of at least any layer among epidermis, dermal papillae, dermis, and subcutaneous tissue that form a skin of the user, and targeting the frequency band in accordance with the layer corresponding to the information concerning the temperature, the modulation unit modulates the control signal such that an influence in accordance with a difference in the temperature of the layer is corrected.

(14)

The information processing device according to any one of (1) to (13), in which the modulation unit temporarily suppresses processing related to modulation of the control signal in accordance with a frequency at which a predetermined state or situation that the context information indicates is changed.

(15)
The information processing device according to any one of (1) to (14), in which
the modulation unit controls a timing at which the control signal is modulated in accordance with a timing at which a predetermined state or situation that the context information indicates is changed.

(16)
The information processing device according to any one of (1) to (15), in which
the context information includes information indicating a plurality of types of states or situations,
the plurality of types of states or situations have been weighted previously, and
the modulation unit modulates the control signal on the basis of the weights set on the plurality of types of states or situations.

(17)
The information processing device according to any one of (1) to (16), in which
the modulation unit modulates the control signal in accordance with a function installed in a predetermined terminal or data held in the terminal.

(18)
The information processing device according to any one of (1) to (17), in which the modulation unit modulates the control signal in accordance with a setting concerning the haptics input in advance.

(19)
The information processing device according to any one of (1) to (18), including:
a control unit configured to present information concerning the haptics presented to the user by the haptics unit on the basis of the control signal after modulation, to the user via a predetermined output unit.

(20)
An information processing method, including:
acquiring, by using a computer system, context information concerning a state or a situation of an external environment or context information concerning a user; and
modulating, by using the computer system, a control signal for controlling a haptics unit for presenting haptics to a predetermined part of the user on the basis of the context information having been acquired.

(21)
A program causing a computer system to execute:
acquiring context information concerning a state or a situation of an external environment or context information concerning a user; and
modulating a control signal for controlling a haptics unit for presenting haptics to a predetermined part of the user on the basis of the context information having been acquired.

REFERENCE SIGNS LIST 1 information processing system
10 information processing device
101 external information analysis unit
103 tactile data analysis unit
105 tactile data modulation unit
107 output control unit
15 storage unit
30 haptics unit
50 external information acquisition device

The invention claimed is:

1. An information processing device comprising:
an acquisition unit configured to acquire context information including at least one of information concerning a state or a situation of an external environment or information concerning a user; and
a modulation unit configured to modulate a control signal for controlling a haptics unit for presenting haptics to a predetermined part of the user based on the context information acquired by the acquisition unit,
wherein the modulation unit modulates the control signal by targeting a plurality of frequency bands and determining a tactile strength of the haptics simultaneously presented at each targeted frequency band of the plurality of targeted frequency bands in accordance with the context information acquired by the acquisition unit,
wherein a combination of respective tactile strengths of the respective haptics simultaneously presented at the plurality of targeted frequency bands is modulated by applying gains to one or more of the targeted frequency bands determined in accordance with the context information,
wherein the context information relates to a tactile sensitivity of the user, and
wherein the acquisition unit and the modulation unit are each implemented via at least one processor.

2. The information processing device according to claim 1, wherein
the context information includes information concerning an age of the user, and
the modulation unit modulates the control signal by targeting at least one frequency band corresponding to the age such that an influence exerted by a difference in the age is corrected.

3. The information processing device according to claim 1, wherein
the context information includes information concerning a sex of the user, and
the modulation unit modulates the control signal such that an influence exerted by a difference in the sex is corrected.

4. The information processing device according to claim 1, wherein
the context information includes information concerning a sensing result of an emotion of the user, and
in a case where the sensing result of the emotion indicates a negative state, the modulation unit modulates the control signal such that an influence exerted by a change in haptics presented to the user by the haptics unit is corrected.

5. The information processing device according to claim 1, wherein
the context information includes information concerning a body temperature of the user, and
the modulation unit modulates the control signal by targeting at least one frequency band corresponding to the body temperature such that an influence exerted by a change in the body temperature is corrected.

6. The information processing device according to claim 1, wherein
the context information includes information concerning an activity volume of the user, and
the modulation unit modulates the control signal by targeting at least one frequency band corresponding to the activity volume such that an influence exerted by a change in the activity volume is corrected.

7. The information processing device according to claim 1, wherein
the context information includes information concerning a heart rate of the user, and
the modulation unit modulates the control signal by targeting at least one frequency band corresponding to the heart rate such that an influence exerted by a change in the heart rate is corrected.

8. The information processing device according to claim 1, wherein
the context information includes information concerning an amount of sweat of the user, and
the modulation unit modulates the control signal by targeting at least one frequency band corresponding to the amount of sweat such that an influence exerted by a change in the amount of sweat is corrected.

9. The information processing device according to claim 1, wherein
the context information includes information concerning brightness of the external environment, and
the modulation unit modulates the control signal such that an influence exerted by a difference in the brightness is corrected.

10. The information processing device according to claim 1, wherein
the context information includes information based on a sound collection result of sound in the external environment, and
targeting the frequency band in accordance with a frequency component included in the sound, the modulation unit modulates the control signal.

11. The information processing device according to claim 1, wherein
the context information includes information concerning a temperature of the external environment, and
the modulation unit modulates the control signal such that an influence exerted by a difference in the temperature is corrected.

12. The information processing device according to claim 1, wherein
the context information includes information concerning a temperature of at least any layer among epidermis, dermal papillae, dermis, and subcutaneous tissue that form a skin of the user, and
targeting the frequency band in accordance with the layer corresponding to the information concerning the temperature, the modulation unit modulates the control signal such that an influence in accordance with a difference in the temperature of the layer is corrected.

13. The information processing device according to claim 1, wherein
the modulation unit temporarily suppresses processing related to modulation of the control signal in accordance with a frequency at which a predetermined state or situation that the context information indicates is changed.

14. The information processing device according to claim 1, wherein
the modulation unit controls a timing at which the control signal is modulated in accordance with a timing at which a predetermined state or situation that the context information indicates is changed.

15. The information processing device according to claim 1, wherein
the context information includes information indicating a plurality of types of states or situations, the plurality of types of states or situations have been weighted previously, and
the modulation unit modulates the control signal based on the weights set on the plurality of types of states or situations.

16. The information processing device according to claim 1, wherein
the modulation unit modulates the control signal in accordance with a function installed in a predetermined terminal or data held in the terminal.

17. The information processing device according to claim 1, comprising:
a control unit configured to present information concerning the haptics presented to the user by the haptics unit based on the control signal after modulation, to the user via a predetermined output unit,
wherein the control unit is implemented via at least one processor.

18. An information processing method, comprising:
acquiring, by using a computer system, context information including at least one of information concerning a state or a situation of an external environment or information concerning a user; and
modulating, by using the computer system, a control signal for controlling a haptics unit for presenting haptics to a predetermined part of the user based on the acquired context information,
wherein the control signal is modulated by targeting a plurality of frequency bands and determining a tactile strength of the haptics simultaneously presented at each targeted frequency band of the plurality of targeted frequency bands in accordance with the acquired context information,
wherein a combination of respective tactile strengths of the respective haptics simultaneously presented at the plurality of targeted frequency bands is modulated by applying gains to one or more of the targeted frequency bands determined in accordance with the context information, and
wherein the context information relates to a tactile sensitivity of the user.

19. A non-transitory computer-readable storage medium having embodied thereon a program, which when executed by a computer system causes the computer system to execute a method, the method comprising:
acquiring context information including at least one of information concerning a state or a situation of an external environment or information concerning a user; and
modulating a control signal for controlling a haptics unit for presenting haptics to a predetermined part of the user based on the acquired context information,
wherein the control signal is modulated by targeting a plurality of frequency bands and determining a tactile strength of the haptics simultaneously presented at each targeted frequency band of the plurality of targeted frequency bands in accordance with the acquired context information,
wherein a combination of respective tactile strengths of the respective haptics simultaneously presented at the plurality of targeted frequency bands is modulated by applying gains to one or more of the targeted frequency bands determined in accordance with the context information, and
wherein the context information relates to a tactile sensitivity of the user.

20. The information processing device according to claim 1, wherein
the modulation unit determines a mix of tactile strengths at the plurality of targeted frequency bands in accordance with weighting of the context information.

21. The information processing device according to claim 20, wherein
the weighting of the context information is performed by setting priorities of a plurality of pieces of information of the context information concerning the state or the situation of the external environment or the context information concerning a user.

* * * * *